(12) United States Patent
Takahashi

(10) Patent No.: US 9,169,187 B2
(45) Date of Patent: Oct. 27, 2015

(54) METHOD OF MAKING PEPTIDES USING DIPHENYLMETHANE COMPOUND

(71) Applicant: AJINOMOTO CO., INC., Tokyo (JP)

(72) Inventor: Daisuke Takahashi, Yokkaichi (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/244,433

(22) Filed: Apr. 3, 2014

(65) Prior Publication Data

US 2014/0213761 A1 Jul. 31, 2014

Related U.S. Application Data

(62) Division of application No. 12/749,980, filed on Mar. 30, 2010, now Pat. No. 8,722,934.

(60) Provisional application No. 61/165,178, filed on Mar. 31, 2009.

(30) Foreign Application Priority Data

Mar. 30, 2009 (JP) ................................ 2009-083579

(51) Int. Cl.
| | | |
|---|---|---|
| *C07K 1/06* | (2006.01) | |
| *C07C 43/205* | (2006.01) | |
| *C07C 43/23* | (2006.01) | |
| *C07C 217/58* | (2006.01) | |
| *C07K 5/113* | (2006.01) | |
| *C07C 217/52* | (2006.01) | |

(52) U.S. Cl.
CPC ............. *C07C 43/2055* (2013.01); *C07C 43/23* (2013.01); *C07C 217/52* (2013.01); *C07C 217/58* (2013.01); *C07K 1/062* (2013.01); *C07K 1/066* (2013.01); *C07K 5/1021* (2013.01); *C07C 2101/14* (2013.01); *C07K 1/06* (2013.01)

(58) Field of Classification Search
CPC ..... C07K 1/062; C07K 1/061; C07C 43/2055
USPC ........................................................ 530/337
See application file for complete search history.

(56) References Cited

U.S. PATENT DOCUMENTS

| | | | |
|---|---|---|---|
| 4,992,576 A | 2/1991 | Gapinski | |
| 5,712,367 A | 1/1998 | Bernard et al. | |
| 7,285,341 B2 | 10/2007 | Zheng et al. | |
| 2005/0202279 A1 | 9/2005 | Zheng et al. | |
| 2006/0135489 A1 | 6/2006 | Matuszczak et al. | |
| 2010/0292439 A1 | 11/2010 | Vaultier et al. | |
| 2012/0059149 A1 | 3/2012 | Takahashi | |
| 2014/0080999 A1 | 3/2014 | Takahashi | |
| 2014/0088291 A1 | 3/2014 | Takahashi | |

FOREIGN PATENT DOCUMENTS

| | | |
|---|---|---|
| GB | 1004218 A1 | 9/1965 |
| GB | 1004281 | 9/1965 |
| JP | 63-188646 | 8/1988 |
| JP | 2579699 | 2/1997 |
| JP | 2000-44493 | 2/2000 |
| JP | 2002-526512 | 8/2002 |
| JP | 2003-533694 A | 11/2003 |
| JP | 2006-306784 A | 11/2006 |
| JP | 2007-537979 A | 12/2007 |
| WO | WO 00/20357 | 4/2000 |
| WO | WO 2006-104166 A1 | 10/2006 |
| WO | WO 2007-034812 A1 | 3/2007 |
| WO | WO 2007/122847 A1 | 11/2007 |
| WO | WO 2008/003836 A1 | 1/2008 |

OTHER PUBLICATIONS

Extended European Search Report issued May 14, 2014 in Patent Application No. 10758710.7.
"2 substances out of 1 citations" Database Reaxys, XP002678988, Jun. 28, 2012, 1 page.
Yoshiki Okamoto, et al., "Photochemical Reaction of [4,(4'-Alkoxybenzoyl)phenylmethyl]phosphonic Acids. Application to a Photo-degradable Surfactant" Chemistry Letters, XP002678989, 1988, pp. 569-572.
Adolf Gogoll, et al., "Photoreaktionen amphiphiler Benzophenon— und Myristinsaurederivate in Micellen und Doppelschichtmembranen" Liebigs Ann. Chem., XP002678990, 1987, pp. 597-606.
F. M. Menger, et al., "Solvolyses of a Carbonate and a Benzhydryl Chloride inside Micelles. Evidence for a Porous Cluster Micelle" Journal of Organic Chemistry, vol. 46, XP002678991, 1981, pp. 415-419.
Peter M. Fischer, et al., "Liquid-phase Peptide Synthesis on Polyethylene Glycol (PEG) Supports using Strategies Based on the 9-fluorenylmethoxycarbonyl Amino Protecting Group: Application of PEGylated Peptides in Biochemical Assays" Journal of Peptide Science, vol. 8, XP002678992, 2002, pp. 529-542.
Kohtaro Goto, et al., "Synthesis of peptides and oligosaccharides by using a recyclable fluorous tag" Tetrahedron Letters, vol. 46, No. 48, XP027863277, Nov. 28, 2005, pp. 8293-8297.
Hitoshi Tamiaki, et al., "A Novel Protecting Group for Constructing Combinatorial Peptide", Bull. Chem. Soc. Jpn. 74, (The Chemical Society of Japan), 2001, pp. 733-738.
Japanese Office Action issued Mar. 3, 2015 in Patent Application No. 2011-507207 (without English Translation).
Wu, Yonggang et al., "Synthesis of Monodisperse spiro-bridged ladder-type oligo-p-pheny lenes", Organic Letters, 2007, vol. 9, No. 22, p. 4435-4438.

*Primary Examiner* — Yong Chu
(74) *Attorney, Agent, or Firm* — Oblon, McClelland, Maier & Neustadt, L.L.P.

(57) ABSTRACT

The present invention aims to provide a compound superior in broad utility and stability, which is useful as a protecting reagent (anchor) of amino acid and/or peptide in liquid phase synthesis and the like of a peptide having a C-terminal etc., which are of a carboxamide (—CONHR)-type, an organic synthesis reaction method (particularly peptide liquid phase synthesis method) using the compound, and a kit for peptide liquid phase synthesis containing the compound, and has found that the object can be achieved by a particular compound having a diphenylmethane skeleton.

21 Claims, No Drawings

METHOD OF MAKING PEPTIDES USING DIPHENYLMETHANE COMPOUND

This application is a Divisional of U.S. application Ser. No. 12/749,980, filed on Mar. 30, 2010, now U.S. Pat. No. 8,722,934, which claims benefit of Provisional application Ser. No. 61/165,178, filed on Mar. 31, 2009.

TECHNICAL FIELD

The present invention relates to a diphenylmethane compound useful as a protecting reagent for organic synthesis reaction, an organic synthesis reaction using the compound and the like. More particularly, it relates to a diphenylmethane compound usable as a protecting reagent for an amino acid or peptide in peptide synthesis, particularly liquid phase synthesis of peptide, and a method of peptide synthesis and organic synthesis using the compound.

BACKGROUND ART

Methods for organic synthesis of compound are generally divided largely into a solid phase method and a liquid phase method. The solid phase method is advantageous in that isolation and purification after the reaction can be performed by only washing of resin. However, the solid phase method is problematic in that it essentially includes a non-homogeneous phase reaction, reaction agents and reagents need to be used in excess amounts to compensate for the low reactivity, and tracking of reaction and analysis of the reaction product on a carrier are difficult.

In an attempt to perform reaction in a homogeneous liquid phase while utilizing the advantage of the solid phase method in that isolation and purification after the reaction can be performed by filtration and washing alone, a method of isolating a particular component dissolved in a liquid as a solid has been used. This is because precipitation of a particular component alone facilitates isolation and purification after reaction.

A particular component dissolved in a solution can be precipitated only when predetermined conditions are satisfied, such as chemical properties, property and relationship with solvents of the compound.

However, determination of precipitation conditions requires trial and error and experimental searches in most cases. In liquid phase synthesis, moreover, some compounds to be synthesized are insoluble in organic solvents used for extraction or show low solubility therein, which necessitates confirmation of the property of each compound to search for isolation and purification methods therefor. Particularly, when sequential and multistep synthesis reactions are required as in peptide synthesis and the like, since isolation and purification conditions such as precipitation, extraction and the like need to be determined based on the properties unique to the compound synthesized in each step, long time and high is cost are required.

In addition, the general liquid phase synthesis process, which has been known for long, requires more complicated operations than the solid phase methods; however, it is advantageous in that intermediate peptide can be purified by extraction wash, isolation and the like after condensation reaction. On the contrary, in extraction wash with nonpolar organic solvents and acidic or basic aqueous solutions, precipitation, transfer to aqueous layer side together with impurity and the like easily occur depending on the chain length and property of peptide, which renders extraction into the organic layer side difficult. Particularly, for a peptide with a short chain having a carboxamide-type C-terminal (—CONHR: R is a hydrogen atom, an alkyl group or an aralkyl group), the difficulty in extraction into an organic layer as mentioned above becomes noticeable since it acquires high hydrophilicity and the like. The peptide having a carboxamide-type C-terminal is generally used for peptide pharmaceutical products for the reasons of stability and improved activity in the body and the like, and causes problems in the liquid phase synthesis of such peptide.

On the other hand, a method using a protecting group (anchor) capable of irreversible change of a dissolution state and an insolubilized state (precipitated state) of a particular component according to the varying solvent composition has been developed. Using such anchor, a compound to be the isolation object can be selectively precipitated from a homogenous solution state.

For example, patent document 1 and non-patent document 1 disclose methods including developing an anchor by introducing a long chain aliphatic group into a benzyl alcohol type compound (see the following structure), dissolving and reacting the anchor in a halogen solvent, and precipitating a reacted product with polar organic solvent such as methanol or acetonitrile to allow peptide chain elongation.

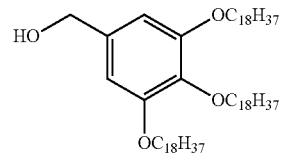

However, since the anchor is a benzyl alcohol type compound, even when the anchor is used as a protecting group of a C-terminal or side chain carboxyl group, the group returns to a free carboxyl group after deprotection. Therefore, the anchor cannot be used as a C-terminal or side chain anchor aiming at synthesis of peptide with carboxamide-type C-terminal.

PRIOR ART REFERENCES

Patent Document patent document 1: JP-A-2000-44493

Non-Patent Document non-patent document 1: Bull. Chem. Soc. Jpn 74, 733-738 (2001)

SUMMARY OF THE INVENTION

Problems to be Solved by the Invention

The present invention aims to provide a compound superior in broad utility and stability, which is useful as a protecting reagent (anchor) for amino acid and/or peptide in liquid phase synthesis and the like of peptide having a carboxamide-type C-terminal or side chain, and an organic synthesis reaction method (particularly peptide liquid phase synthesis method) using the compound, as well as a kit for liquid phase synthesis of peptide, which contains the compound.

Means of Solving the Problems

The present inventor has conducted intensive studies in view of the above-mentioned problems and found that a particular compound having a diphenylmethane skeleton can solve the above-mentioned problems and completed the present invention. Accordingly, the present invention is as described below.

[1] A diphenylmethane compound represented by the formula (I):

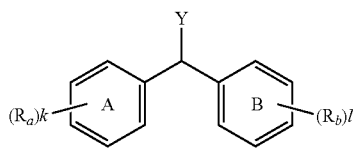

wherein
Y is a hydroxyl group or a —NHR group (R is a hydrogen atom, an alkyl group or an aralkyl group);
k and l are each independently an integer of 0-5 and k+l is not 0;
$R_a$ in the number of k and $R_b$ in the number of l are each independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
ring A optionally further has substituent(s) besides $R_a$; and
ring B optionally further has substituent(s) besides $R_b$.
[2] The diphenylmethane compound of the above-mentioned [1], wherein, in the organic group(s) in the number of (k+l), the total carbon number of the aliphatic hydrocarbon groups is 16-200.
[3] The diphenylmethane compound of the above-mentioned [1] or [2], wherein the aliphatic hydrocarbon group independently has a carbon number of not less than 5.
[4] The diphenylmethane compound of the above-mentioned [1] or [2], wherein the aliphatic hydrocarbon group independently has a carbon number of 5-60.
[5] The diphenylmethane compound of any of the above-mentioned [1] to [4], wherein the organic group is independently bonded directly to ring A or ring B by a carbon-carbon bond or via —O—, —S—, —COO—, —OCONH— or —CONH—.
[6] The diphenylmethane compound of the above-mentioned [5], wherein the organic group is bonded to the 4-position of ring A or ring B via —O—.
[7] The diphenylmethane compound of any of the above-mentioned [1] to [4], wherein the organic group having an aliphatic hydrocarbon group is independently selected from a group represented by the formula (a):

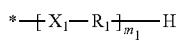

wherein
* shows the position of a bond;
$m_1$ is an integer of 1-10;
$X_1$ in the number of $m_1$ are each independently absent or —O—, —S—, —COO—, —OCONH— or —CONH—; and
$R_1$ in the number of $m_1$ are each independently divalent aliphatic hydrocarbon groups having a carbon number of not less than 5, a group represented by the formula (b):

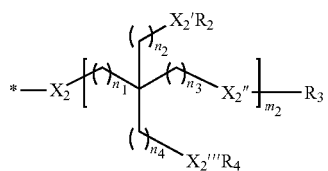

wherein
* shows the position of a bond;
$m_2$ is an integer of 1 or 2;
$n_1, n_2, n_3$ and $n_4$ in the number of $m_2$ are each independently an integer of 0-2;
$X_2, X_2'$ in the number of $m_2$, $X_2''$ in the number of $m_2$ and $X_2'''$ in the number of $m_2$ are each independently absent, or —O—, —S—, —COO—, —OCONH— or —CONH—;
$R_2$ and $R_4$ in the number of $m_2$ are each independently a hydrogen atom, a methyl group or an aliphatic hydrocarbon group having a carbon number of not less than 5; and
$R_3$ is an aliphatic hydrocarbon group having a carbon number of not less than 5, and
a group represented by the formula (e):

wherein
* shows the position of a bond;
$m_3$ is an integer of 0-15;
$n_5$ is an integer of 0-11;
$n_6$ is an integer of 0-5;
$X_8$ is absent or —O—, —S—, —NHCO— or —CONH—;
$X_7$ in the number of $m_3$ are each independently absent or —O—, —S—, —COO—, —OCONH—, —NHCO— or —CONH—; and
$R_{12}$ in the number of $m_3$ are each independently a hydrogen atom, a methyl group or an aliphatic hydrocarbon group having a carbon number of not less than 5.
[8] The diphenylmethane compound of the above-mentioned [7], wherein, in the formula (a),
$m_1$ is 1 or 2;
$X_1$ is —O—; and
$R_1$ is a divalent aliphatic hydrocarbon group having a carbon number of 5-60.
[9] The diphenylmethane compound of the above-mentioned [7], wherein, in the formula (b),
$m_2$ is 1;
$n_1, n_2, n_3$ and $n_4$ are each independently an integer of 0-1;
$X_2$ is —O— or —CONH—;
$X_2', X_2''$ and $X_2'''$ are each independently absent or —O—;
$R_2$ and $R_4$ are each independently a hydrogen atom, a methyl group or an aliphatic hydrocarbon group having a carbon number of 5-60; and
$R_3$ is an aliphatic hydrocarbon group having a carbon number of 5-60.
[10] The diphenylmethane compound of the above-mentioned [7], wherein, in the formula (e),
$m_3$ is 2 or 3;
$n_5$ is 1;
$n_6$ is 2 or 3;

$X_8$ is —O—;
$X_7$ is —O—; and
$R_{12}$ in the number of $m_3$ are each independently an alkyl group having a carbon number of 8-60.

[11] The diphenylmethane compound of any of the above-mentioned [1] to [10], wherein Y is a hydroxyl group.

[12] The diphenylmethane compound of the above-mentioned [7], wherein Y is a hydroxyl group;
k and l are each independently an integer of 0-3; and
the organic group having an aliphatic hydrocarbon group is present at the 4-position of the ring A or ring B and is represented by the formula (a) wherein $m_1$ is 1 or 2; $X_1$ is —O—; and $R_1$ is a divalent aliphatic hydrocarbon group having a carbon number of 5-60, or the formula (e) wherein $m_3$ is 2 or 3; $n_5$ is 1; $n_6$ is 2 or 3; $X_8$ is —O—; $X_7$ is —O—; and $R_{12}$ in the number of $m_3$ are each independently an alkyl group having a carbon number of 14-30.

[13] The diphenylmethane compound of any of the above-mentioned [1] to [10], wherein Y is a —NHR group (R is a hydrogen atom, an alkyl group or an aralkyl group).

[14] The diphenylmethane compound of the above-mentioned [7], wherein Y is a —NHR group (R is a hydrogen atom, an alkyl group or an aralkyl group;
k and l are each independently an integer of 0-3;
the organic group having an aliphatic hydrocarbon group is present at the 4-position of the ring A or ring B and is represented by the formula (a) wherein $m_1$ is 1 or 2; $X_1$ is —O—; and $R_1$ is a divalent aliphatic hydrocarbon group having a carbon number of 5-60, or a group represented by the formula (e) wherein $m_3$ is 2 or 3; $n_5$ is 1; $n_6$ is 2 or 3; $X_8$ is —O—; $X_7$ is —O—; and $R_{12}$ in the number of $m_3$ are each independently an alkyl group having a carbon number 14-30.

[15] The diphenylmethane compound of the above-mentioned [7], which is selected from the group consisting of 2,3,4-trioctadecanoxybenzhydrol; [phenyl(2,3,4-trioctadecanoxyphenyl)methyl]amine; 4,4'-didocosoxybenzhydrol; di(4-docosoxyphenyl)methylamine; 4,4-di(12-docosoxy-dodecyloxy)benzhydrol; amino-bis[4-(12-docosoxydodecyloxy)phenyl]methane; N-benzyl-[bis(4-docosyloxyphenyl)]methylamine; (4-methoxy-phenyl)-[4-(3,4,5-tris-octadecyloxy-cyclohexylmethoxy)-phenyl]-methanol; {(4-methoxy-phenyl)-[4-(3,4,5-tris-octadecyloxy-cyclohexylmethoxy)-phenyl]-methyl}-amine; and [bis-(4-docosoxy-phenyl)-methyl]-amine.

[16] A protecting reagent for a —CONHR group (R is a hydrogen atom, an alkyl group or an aralkyl group), comprising the diphenylmethane compound of the above-mentioned [11] or [12].

[17] A protecting reagent for a —CONHR group (R is a hydrogen atom, an alkyl group or an aralkyl group) comprising the diphenylmethane compound of the above-mentioned [13] or [14], which converts a —COOH group to a protected —CONHR group.

[18] A conversion reagent for converting a —COOH group to a —CONHR group (R is a hydrogen atom, an alkyl group or an aralkyl group) comprising the diphenylmethane compound of the above-mentioned [13] or [14].

[19] A protecting reagent for amino acid or peptide having a —CONHR group (R is a hydrogen atom, an alkyl group or an aralkyl group), comprising the diphenylmethane compound of the above-mentioned [11] or [12].

[20] A protecting reagent comprising the diphenylmethane compound of the above-mentioned [13] or [14], which converts a —COOH group of amino acid or peptide to a protected —CONHR(R is a hydrogen atom, an alkyl group or an aralkyl group) group.

[21] A method of producing peptide by a liquid phase synthesis process comprising the following steps;
(1) a step of condensing the diphenylmethane compound of the above-mentioned [11] or [12] with a —CONHR (R is a hydrogen atom, an alkyl group or an aralkyl group) group of an N-protected amino acid or N-protected peptide having a —CONHR group, or condensing the diphenylmethane compound of the above-mentioned [13] or [14] with a —COOH group of an N-protected amino acid or N-protected peptide having a —COOH group to give C-diphenylmethane-protected amino acid or C-diphenylmethane-protected peptide (diphenylmethane protection step),
(2) a step of deprotecting the N-terminal of the amino acid or peptide obtained in the above-mentioned step (N-terminal deprotection step),
(3) a step of condensing the N-terminal of the amino acid or peptide obtained in the above-mentioned step with N-protected amino acid or N-protected peptide (peptide chain elongation step), and
(4) a step of precipitating the peptide obtained in the above-mentioned step (precipitation step).

[22] The method of the above-mentioned [16], further comprising one or more repeats of the following steps (5)-(7);
(5) a step of deprotecting the N-terminal of the peptide obtained in the precipitation step (N-terminal deprotection step),
(6) a step of condensing the N-terminal of peptide obtained in the above-mentioned step with N-protected amino acid or N-protected peptide (peptide chain elongation step), and
(7) a step of precipitating the peptide obtained in the above-mentioned step (precipitation step).

[23] The production method of the above-mentioned [16] or [17], further comprising the following step (8);
(8) a step of removing a group represented by the formula (I-d):

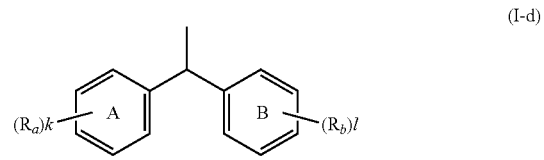

wherein
k and l are each independently an integer of 0-5 and k+l is not 0;
$R_a$ in the number of k and $R_b$ in the number of l are each independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
ring A optionally further has substituent(s) besides $R_a$; and
ring B optionally further has substituent(s) besides $R_b$, from the peptide obtained in the precipitation step to give a carboxamide-type peptide.

[24] A method of producing a peptide compound, comprising using the diphenylmethane compound of any of the above-mentioned [1] to [15].

[25] A method of producing an organic compound, comprising using the diphenylmethane compound of any of the above-mentioned [1] to [15].

[26] A method of producing a diphenylmethane compound represented by the formula (I-a):

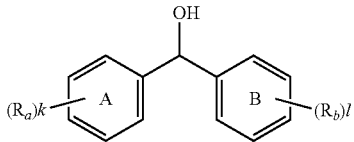
(I-a)

wherein k and l are each independently an integer of 0-5 and k+l is not 0;

$R_a$ in the number of k and $R_b$ in the number of l are each independently an organic group having an aliphatic hydrocarbon group, wherein, in the organic group(s) in the number of (k+l), each having an aliphatic hydrocarbon group, the total carbon number of the aliphatic hydrocarbon groups is not less than 16;

ring A optionally further has substituent(s) besides $R_a$; and ring B optionally further has substituent(s) besides $R_b$, comprising a step of reducing a benzophenone compound represented by the formula (II):

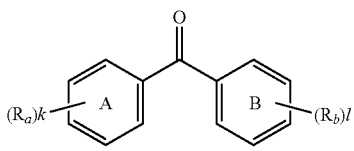
(II)

wherein each symbol is as defined above.

[27] A method of producing a diphenylmethane compound represented by the formula (I-b):

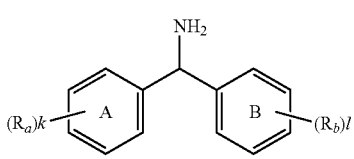
(I-b)

wherein k and l are each independently an integer of 0-5 and k+l is not 0;

$R_a$ in the number of k and $R_b$ in the number of l are each independently an organic group having an aliphatic hydrocarbon group, wherein, in the organic group(s) in the number of (k+l), each having an aliphatic hydrocarbon group, the total carbon number of the aliphatic hydrocarbon groups is not less than 16;

ring A optionally further has substituent(s) besides $R_a$; and ring B optionally further has substituent(s) besides $R_b$, comprising a step of reacting a diphenylmethane compound represented by the formula (I-a):

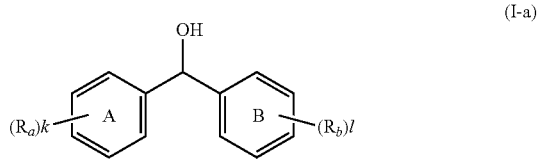
(I-a)

wherein each symbol is defined above, with a compound having a —$CONH_2$ group or a —$OCONH_2$ group, and treating the resulting compound with a base.

[28] A method of producing a diphenylmethane compound represented by the formula (I-b):

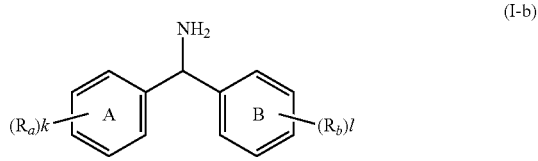
(I-b)

wherein k and l are each independently an integer of 0-5 and k+l is not 0;

$R_a$ in the number of k and $R_b$ in the number of l are each independently an organic group having an aliphatic hydrocarbon group, wherein, in the organic group(s) in the number of (k+l), each having an aliphatic hydrocarbon group, the total carbon number of the aliphatic hydrocarbon groups is not less than 16;

ring A optionally further has substituent(s) besides $R_a$; and ring B optionally further has substituent(s) besides $R_b$, comprising chlorinating or brominating a diphenylmethane compound represented by the formula (I-a):

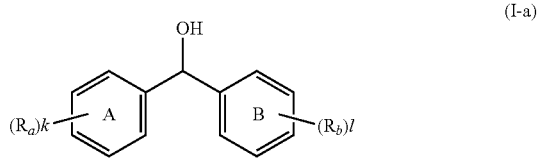
(I-a)

wherein the symbols are as defined above, to give a diphenylmethane compound represented by the formula (I'-a):

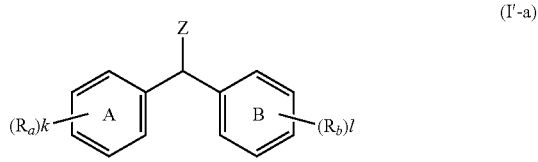
(I'-a)

wherein Z is a chlorine atom or a bromine atom, and other symbols are as defined above, azidating the compound to give a diphenylmethane compound represented by the formula (I'-b):

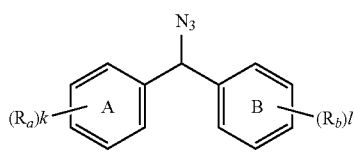

(I'-b)

wherein the symbols are as defined above, and aminating the compound.

[29] A method of producing a diphenylmethane compound represented by the formula (I-c):

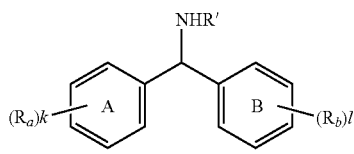

(I-c)

wherein k and l are each independently an integer of 0-5 and k+l is not 0;

$R_a$ in the number of k and $R_b$ in the number of l are each independently an organic group having an aliphatic hydrocarbon group, wherein, in the organic groups in the number of (k+l), each having an aliphatic hydrocarbon group, the total carbon number of the aliphatic hydrocarbon groups is not less than 16;

ring A optionally further has substituent(s) besides $R_a$; and
ring B optionally further has substituent(s) besides $R_b$;

Z is a chlorine atom or a bromine atom, comprising a step of reacting a diphenylmethane compound represented by the formula (I'-a):

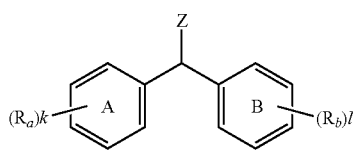

(I'-a)

wherein each symbol is as defined above, with R'—NH$_2$ (R' is an alkyl group or an aralkyl group).

Effect of the Invention

The compound of the present invention is superior in broad utility and stability in organic synthesis reactions, particularly peptide liquid phase synthesis reactions. When the compound of the present invention is subjected to a peptide liquid phase synthesis as a protecting reagent (anchor), a peptide having a C-terminal etc., which are of a carboxamide type, is obtained by an easy operation such as reaction, precipitation and the like.

Using the particular compound having a diphenylmethane skeleton of the present invention, a compound superior in broad utility and stability, which is useful as a protecting reagent (anchor) of amino acid and/or peptide in liquid phase synthesis and the like of a peptide having a carboxamide-type C-terminal or side chain, an organic synthesis reaction method (particularly peptide liquid phase synthesis method) using the compound, and a kit for peptide liquid phase synthesis containing the compound can be provided.

In other words, since the particular compound having a diphenylmethane skeleton dissolves only in halogen solvents, THF and the like, and scarcely dissolves in polar organic solvents, the compound can be easily precipitated in methanol and the like. In addition, peptide chain length can be elongated by repeating an operation including reaction in a halogen solvent using the compound as an anchor of the C-terminal or side chain (hereinafter to be also referred collectively to as "C-terminal etc." in the present specification) during peptide liquid phase synthesis, followed by precipitation with methanol etc. to remove impurities. Furthermore, after deprotection by setting acidic conditions and the like, the C-terminal etc. can be led to carboxamide.

EMBODIMENT OF THE INVENTION

Unless otherwise specified in the sentences, any technique terms and scientific terms used in the present specification, have the same meaning as those generally understood by those of ordinary skill in the art in the art the present invention belongs to. Any methods and materials similar or equivalent to those described in the present specification can be used for practicing or testing the present invention, and preferable methods and materials are described in the following. All publications and patents referred to in the Specification are hereby incorporated by reference so as to describe and disclose constructed products and methodology described in, for example, Publications usable in relation to the described invention.

1. The Compound of the Present Invention

The compound of the present invention is useful as a reagent for organic synthesis. Here, the reagent for organic synthesis refers to any reagent relating to organic synthesis reactions, and is a concept including reagents directly involved in the reaction such as reactive substrate, reaction promoter, reagent for introducing protecting group, deprotecting agent and the like, as well as inert solvent and the like. Specifically, reagents to be used for peptide synthesis reaction are exemplified. Preferred is a reagent introduced as a protecting group (anchor) of the C-terminal of amino acid or peptide in liquid phase synthesis of peptide, and an appropriate compound can be selected according to the object. Particularly preferable compound of the present invention is an anchor.

One embodiment of the compound of the present invention is a diphenylmethane compound represented by the following formula (I):

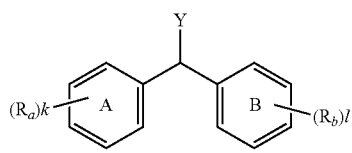

(I)

wherein

Y is a hydroxyl group or a —NHR group (R is a hydrogen atom, an alkyl group or an aralkyl group);

k and l are each independently an integer of 0-5 and k+l is not 0;

$R_a$ in the number of k and $R_b$ in the number of l are each independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
ring A optionally further has substituent(s) besides $R_a$; and ring B optionally further has substituent(s) besides $R_b$.

The compound represented by the formula (I) in the present invention (hereinafter to be abbreviated as the compound of the present invention) is bonded, via a Y group, to a compound to be protected.

Here, the compound of the present invention wherein Y is a hydroxyl group is protected by binding with a compound having a —CONHR group, and a group represented by the formula (I-d):

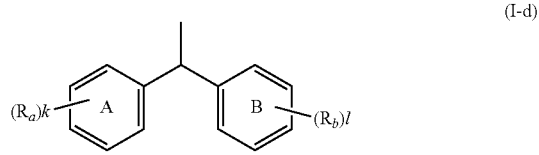

(I-d)

wherein each symbol is as defined above, is removed by a treatment with acid and the like to give a compound having a —CONHR group. In other words, the compound of the present invention can be applied as a protecting group of a —CONHR group.

On the other hand, the compound of the present invention wherein Y is a —NHR group is bound with a compound having a —COOH group so as to convert the —COOH group to a protected —CONHR group. Then, a group represented by the formula (I-d) is removed by a treatment with acid and the like to give a compound having a —CONHR group. In other words, the compound of the present invention can be applied to protect and deprotect the —COOH group for final conversion to a —CONHR group.

In the peptide liquid phase synthesis, when the compound of the present invention is applied as an anchor of C-terminal etc. of amino acid or peptide, the compound of the present invention wherein Y is a hydroxyl group is applied to amino acid or peptide wherein C-terminal etc. are a —CONHR group, and the compound of the present invention wherein Y is a —NHR group (R is a hydrogen atom, an alkyl group or an aralkyl group) is applied to amino acid or peptide wherein C-terminal etc. are a —COOH group. Therefore, the compound of the present invention is a protecting reagent (anchor) highly useful for the synthesis of peptide having a C-terminal etc. in its final form, which are of a carboxamide type.

In the present specification, examples of the "alkyl group" for R include a $C_{1-30}$ alkyl group, preferably a $C_{1-10}$ alkyl group, more preferably a $C_{1-6}$ alkyl group. Preferable examples include methyl, ethyl, propyl, isopropyl, butyl, isobutyl, sec-butyl, tert-butyl, pentyl, hexyl and the like, and particularly preferred are methyl and ethyl.

In the present specification, examples of the "aralkyl group" for R include a $C_{7-30}$ aralkyl group. Preferred is a $C_{7-20}$ aralkyl group, more preferred is a $C_{7-16}$ aralkyl group (a $C_{6-10}$ aryl-$C_{1-6}$ alkyl group). Preferable examples include benzyl, 1-phenylethyl, 2-phenylethyl, 1-phenylpropyl, naphthylmethyl, 1-naphthylethyl, 1-naphthylpropyl and the like, and particularly preferred is benzyl.

As R, a hydrogen atom, a $C_{1-6}$ alkyl group or a $C_{7-16}$ aralkyl group is preferable, a hydrogen atom, methyl, ethyl or benzyl is more preferable, and a hydrogen atom is particularly preferable.

In the present specification, examples of the "substituent" which ring A or ring B further optionally has include those generally used in the field. Preferable examples include an alkyl group (e.g., $C_{1-6}$ alkyl group such as methyl, ethyl, propyl, isopropyl, butyl, isobutyl, sec-butyl, tert-butyl, pentyl, hexyl etc.), an alkoxy group (e.g., $C_{1-6}$ alkoxy group such as methoxy, ethoxy, propoxy, isopropoxy, butoxy, isobutoxy, sec-butoxy, tert-butoxy, pentyloxy, hexyloxy etc.) and the like. Preferably, ring A and ring B do not have a "substituent", or when they have, an alkoxy group is particularly preferable as the substituent.

In the present specification, the "organic group having an aliphatic hydrocarbon group" means a monovalent organic group (one bond is bonded to ring A and/or ring B) which has an aliphatic hydrocarbon group in the molecular structure.

The "aliphatic hydrocarbon group" of the "organic group having an aliphatic hydrocarbon group" is a straight chain or branched, saturated or unsaturated aliphatic hydrocarbon group, and an aliphatic hydrocarbon group having a carbon number of not less than 5 is preferable, an aliphatic hydrocarbon group having a carbon number of 5-60 is particularly preferable, an aliphatic hydrocarbon group having a carbon number of 5-30 is more preferable, and an aliphatic hydrocarbon group having a carbon number of 10-30 is further preferable.

The moiety of the "aliphatic hydrocarbon group" in the "organic group having an aliphatic hydrocarbon group" of is not particularly limited, and it may be present at the terminal (monovalent group), or other site (e.g., divalent group).

Specific examples of the "aliphatic hydrocarbon group" include monovalent groups such as methyl group, ethyl group, propyl group, isopropyl group, butyl group, isobutyl group, sec-butyl group, tert-butyl group, pentyl group, hexyl group, octyl group, decyl group, lauryl group, tridecyl group, myristyl group, cetyl group, stearyl group, arachyl group, behenyl group, oleyl group, isostearyl group and the like and a divalent group derived therefrom.

In the "organic group having an aliphatic hydrocarbon group", a moiety other than the "aliphatic hydrocarbon group" can be set freely. For example, it optionally has a moiety such as —O—, —S—, —COO—, —OCONH—, —CONH—, hydrocarbon group (monovalent or divalent) and the like. Examples of the "hydrocarbon group" include aliphatic hydrocarbon group, monocyclic saturated hydrocarbon group and aromatic hydrocarbon group and the like, specific examples include a monovalent group such as alkyl group, alkenyl group, alkynyl group, cycloalkyl group, aryl group, aralkyl group and the like and a divalent group derived therefrom. Examples of the "alkyl group" include $C_{1-6}$ alkyl group and the like and preferable examples include methyl, ethyl, propyl, isopropyl, butyl, isobutyl, sec-butyl, tert-butyl, pentyl, hexyl and the like. Examples of the "alkenyl group" include $C_{2-6}$ alkenyl group and the like and preferable examples include vinyl, 1-propenyl, allyl, isopropenyl, butenyl, isobutenyl and the like. Examples of "alkynyl group" include $C_{2-6}$ alkynyl group and the like and preferable examples include ethynyl, propargyl, 1-propynyl and the like. Examples of the "cycloalkyl group" include $C_{3-6}$ cycloalkyl group and the like and preferable examples include cyclopropyl, cyclobutyl, cyclopentyl and cyclohexyl. The "aryl group" is preferably, for example, $C_{6-14}$ aryl group and the like. For example, phenyl, 1-naphthyl, 2-naphthyl, biphenylyl, 2-anthryl and the like are included. Among these, a $C_{6-10}$ aryl group is more preferable, and phenyl is particularly preferable. As the "aralkyl group", for example, a $C_{7-20}$ aralkyl group is preferable. Examples include benzyl, 1-phenylethyl, 2-phenylethyl, 1-phenylpropyl, naphthylmethyl, 1-naphthylethyl, 1-naphthylpropyl and the like. Among these, a $C_{7-16}$ aralkyl group ($C_{6-10}$ aryl-$C_{1-6}$ alkyl group) is more preferable, and benzyl is particularly preferable. The hydrocarbon group is optionally substituted by a substituent selected from a halogen atom (chlorine atom, bromine atom, fluorine atom, iodine atom), an oxo group and the like.

The "organic group having an aliphatic hydrocarbon group" may be bonded (substituted) to ring A and/or ring B via "an aliphatic hydrocarbon group" present in the group or the above-mentioned "hydrocarbon group", namely, directly bonded to form a carbon-carbon bond or via —O—, —S—, —COO—, —OCONH—, —CONH— and the like present in the group. Preferably, it is bonded via —O—, —S—, —COO— or —CONH— in view of the easiness of synthesis of the compound. More preferably, it is bonded via —O—.

In the compound of the present invention, ring A and ring B have the "organic group having an aliphatic hydrocarbon group" in the number of (k+l) (not 0), preferably 1 to 4, preferably 1 to 3, more preferably 1 or 2, in total. Here, all "organic groups having an aliphatic hydrocarbon group" may be present on the same ring or different rings. In addition, one "organic group having an aliphatic hydrocarbon group" may have a plurality of the "aliphatic hydrocarbon group" by branching and the like. When the "organic group having an aliphatic hydrocarbon group" has plural "aliphatic hydrocarbon groups", they may be the same or different.

When the "organic group having an aliphatic hydrocarbon group" is bonded via —O—, at least one of the "organic groups having an aliphatic hydrocarbon group" is preferably bonded to the 4-position of ring A and/or ring B since its removal is easy.

In the compound of the present invention, in the organic group(s) in the number of (k+l), each having an aliphatic hydrocarbon group, the total carbon number of the aliphatic hydrocarbon group(s) is not less than 16. Preferred is 16-200, more preferred is 16-100, and further preferred is 16-60. A higher carbon number produces good crystallinity of the compound of the present invention in a polar organic solvent even when the peptide chain is long.

The "aliphatic hydrocarbon group" in the "organic group having an aliphatic hydrocarbon group" is appropriately selected according to the use of the compound to be synthesized. For example, when it is used as an anchor at the C-terminal of an amino acid or peptide, one having a comparatively long chain length, namely, one having a carbon number of not less than 5 is preferably employed. Furthermore, an aliphatic hydrocarbon group having a carbon number of 5-60 is more preferable, an aliphatic hydrocarbon group having a carbon number of 5-30 is further preferable, and an aliphatic hydrocarbon group having a carbon number of 10-30 is still more preferable.

Examples of the "organic group having an aliphatic hydrocarbon group" include groups represented by the following formulas (a)-(e)

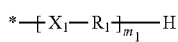
(a)

in the formula (a),
* shows the position of a bond;
$m_1$ is an integer of 1-10;
$X_1$ in the number of $m_1$ are each independently absent or —O—, —S—, —COO—, —OCONH— or —CONH—;

$R_1$ in the number of $m_1$ are each independently a divalent aliphatic hydrocarbon group having a carbon number of not less than 5.

As the "aliphatic hydrocarbon group having a carbon number of not less than 5" for $R_1$, an "aliphatic hydrocarbon group" of the above-mentioned "organic group having an aliphatic hydrocarbon group", which has a carbon number of not less than 5, can be mentioned, with preference given to one having a carbon number of 5-60.

In the formula (a),
a group wherein
$m_1$ is 1;
$X_1$ is —O—; and
$R_1$ is a divalent aliphatic hydrocarbon group having a carbon number of 5-60
is particularly preferable.

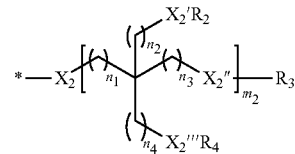
(b)

in the formula (b),
* shows the position of a bond;
$m_2$ is an integer of 1 or 2;
$n_1, n_2, n_3$ and $n_4$ in the number of $m_2$ are each independently an integer of 0-2;
$X_2$, $X_2'$ in the number of $m_2$, $X_2''$ in the number of $m_2$ and $X_2'''$ in the number of $m_2$ are each independently absent, or —O—, —S—, —COO—, —OCONH— or —CONH—;
$R_2$ and $R_4$ in the number of $m_2$ are each independently a hydrogen atom, a methyl group or an aliphatic hydrocarbon group having a carbon number of not less than 5; and
$R_3$ is an aliphatic hydrocarbon group having a carbon number of not less than 5.

As the "aliphatic hydrocarbon group having a carbon number of not less than 5" for $R_2$, $R_3$ or $R_4$, an "aliphatic hydrocarbon group" of the above-mentioned "organic group having an aliphatic hydrocarbon group", which has a carbon number of not less than 5, can be mentioned, with preference given to one having a carbon number of 5-60.

In the formula (b),
a group wherein
$m_2$ is 1;
$n_1, n_2, n_3$ and $n_4$ are each independently an integer of 0-1;
$X_2$ is —O— or —CONH—;
$X_2'$, $X_2''$ and $X_2'''$ are each independently absent or —O—;
$R_2$ and $R_4$ are each independently a hydrogen atom, a methyl group or an aliphatic hydrocarbon group having a carbon number of 5-60; and
$R_3$ is an aliphatic hydrocarbon group having a carbon number of 5-60
is particularly preferable.

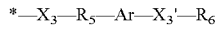
(c)

in the formula (c),
* shows the position of a bond;
$X_3$ and $X_3'$ are each independently absent, or —O—, —S—, —COO—, —OCONH— or —CONH—;
$R_5$ and $R_6$ are each independently an aliphatic hydrocarbon group; and
Ar is an arylene group.

Examples of the "aliphatic hydrocarbon group" for $R_5$ or $R_6$ include those similar to the "aliphatic hydrocarbon group" of the above-mentioned "organic group having an aliphatic hydrocarbon group". The carbon number is preferably not less than 5, more preferably 5-60.

Examples of the "arylene group" for Ar include phenylene, naphthylene, biphenylene and the like, with preference given to phenylene.

In the formula (c),
a group wherein
$X_3$ and $X_3'$ are each —O—;
$R_5$ and $R_6$ are each an aliphatic hydrocarbon group having a carbon number of 5-60; and
Ar is phenylene
is particularly preferable.

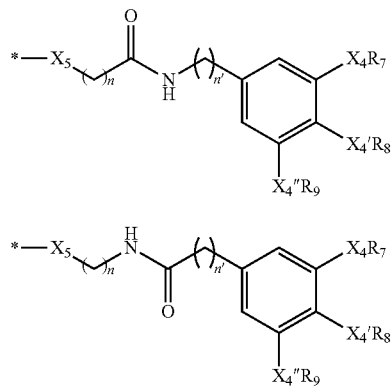

in the formula (d),
* shows the position of a bond;
n and n' are each independently an integer of 0-20;
$X_4$, $X_4'$ and $X_4''$ are each independently absent or —O—, —S—, —COO—, —OCONH— or —CONH—;
$X_5$ is absent or —O—; and
$R_7$, $R_8$ and $R_9$ are each independently an aliphatic hydrocarbon group.

Examples of the "aliphatic hydrocarbon group" for $R_7$, $R_8$ or $R_9$ include those similar to the "aliphatic hydrocarbon group" of the above-mentioned "organic group having an aliphatic hydrocarbon group". The carbon number is preferably not less than 5, more preferably 5-60, particularly preferably 5-30.

In the formula (d),
a group wherein
n is an integer of 0-20;
$X_4$, $X_4'$ and $X_{41}''$ are each —O—; and
$R_7$, $R_8$ and $R_9$ are each independently an aliphatic hydrocarbon group having a carbon number of 5-30
is particularly preferable.

wherein * shows the position of a bond; $X_8$ is absent or —O—, —S—, —NHCO— or —CONH—; $m_3$ is an integer of 0-15; $n_5$ is an integer of 0-11; $n_6$ is an integer of 0-5; $X_7$ is absent or —O—, —S—, —COO—, —OCONH—, —NHCO— or —CONH—; $R_{12}$ is a hydrogen atom, a methyl group or an aliphatic hydrocarbon group having a carbon number of not less than 5; when $X_7$ is present in plurality, respective $X_7$ may be the same or different; and when $R_{12}$ is present in plurality, respective $R_{12}$ may be the same or different.

As the "aliphatic hydrocarbon group having a carbon number of not less than 5" for $R_{12}$, the "aliphatic hydrocarbon group" of the above-mentioned "organic group having an aliphatic hydrocarbon group" having a carbon number of not less than 5 can be mentioned, preferably one having a carbon number of 5-80.

In the formula (e), a group wherein $X_8$ is —O—; $m_3$ is 2 or 3; $n_5$ is 1; $n_6$ is 2 or 3; $X_7$ is —O—; and $R_{12}$ in the number of $m_3$ show each independently an alkyl group having a carbon number of 8-60, is preferable.

Specific examples of the "organic group having an aliphatic hydrocarbon group" from among aliphatic carbon chain groups having a carbon number of 18 or 22 include the following. In each group, * shows the position of a bond.

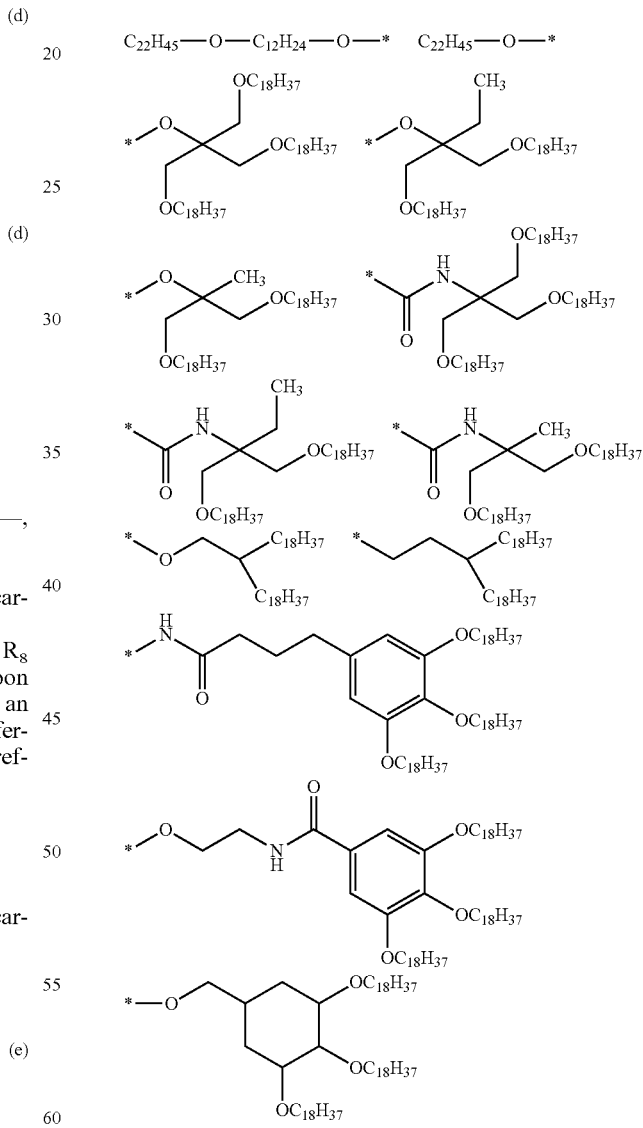

In addition, the following group is also used.

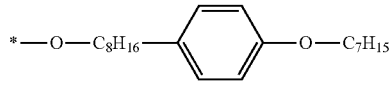

As the diphenylmethane compound represented by the formula (I) of the present invention, preferred is a compound represented by the formula (I),
wherein
Y is a hydroxyl group;
k and l are each independently an integer of 0-3; and
the organic group having an aliphatic hydrocarbon group is a group represented by the formula (a) wherein $m_1$ is 1 or 2; $X_1$ is —O—; and $R_1$ is a divalent aliphatic hydrocarbon group having a carbon number of 5-60, or a group represented by the formula (e) wherein $m_3$ is 2 or 3; $n_5$ is 1; $n_6$ is 2 or 3; $X_8$ is —O—; $X_7$ is —O—; and $R_{12}$ in the number of $m_3$ is each independently to an alkyl group having a carbon number of 14-30, which is present at the 4-position of ring A or ring B.

Furthermore, as another embodiment of the diphenylmethane compound of the present invention represented by the formula (I), preferred is a compound of the formula (I), wherein
Y is a —NHR group (R is a hydrogen atom, an alkyl group or an aralkyl group);
k and l are each independently an integer of 0-3; and the organic group having an aliphatic hydrocarbon group is a group represented by the formula (a) wherein $m_1$ is 1 or 2; $X_1$ is —O—; and $R_1$ is a divalent aliphatic hydrocarbon group having a carbon number of 5-60, or a group represented by the formula (e) wherein $m_3$ is 2 or 3; $n_5$ is 1; $n_6$ is 2 or 3; $X_8$ is —O—; $X_7$ is —O—; and $R_{12}$ in the number of $m_3$ is each independently an alkyl group having a carbon number of 14-30, which is present at the 4-position of ring A or ring B.

Preferable examples of the diphenylmethane compound of the present invention include the following diphenylmethane compounds.

2,3,4-trioctadecanoxybenzhydrol;
[phenyl(2,3,4-trioctadecanoxyphenyl)methyl]amine;
4,4'-didocosoxybenzhydrol;
di(4-docosoxyphenyl)methylamine;
4,4-di(12-docosoxydodecyloxy)benzhydrol;
amino-bis[4-(12-docosoxydodecyloxy)phenyl]methane;
N-benzyl-[bis(4-docosyloxyphenyl)]methylamine;
(4-methoxy-phenyl)-[4-(3,4,5-tris-octadecyloxy-cyclohexylmethoxy)-phenyl]-methanol;
{(4-methoxy-phenyl)-[4-(3,4,5-tris-octadecyloxy-cyclohexylmethoxy)-phenyl]-methyl}-amine; and
[bis-(4-docosoxy-phenyl)-methyl]-amine.

2. Production Method of the Compound of the Present Invention

While the production method of the compound of the present invention is not particularly limited, it can be synthesized, for example, via the following reactions.

Unless otherwise specified, the starting compound may be a commercially available product, or can be produced according to a method known per se or a method analogous thereto.

While the yield of the compound obtained by each of the following methods may vary depending on the reaction conditions employed, the compound can be isolated and purified from the resulting product by a general method (recrystallization, column chromatography and the like), and then precipitated by a method of changing the solution temperature, a method of changing the solution composition and the like.

In each reaction, when the starting compound has a hydroxy group, an amino group, a carboxy group or a carbonyl group, a protecting group generally used in the peptide chemistry and the like may be introduced into these groups, and the object compound can be obtained by removing the protecting group as necessary after the reaction.

The compound of the present invention can be produced, for example, according to the following steps.

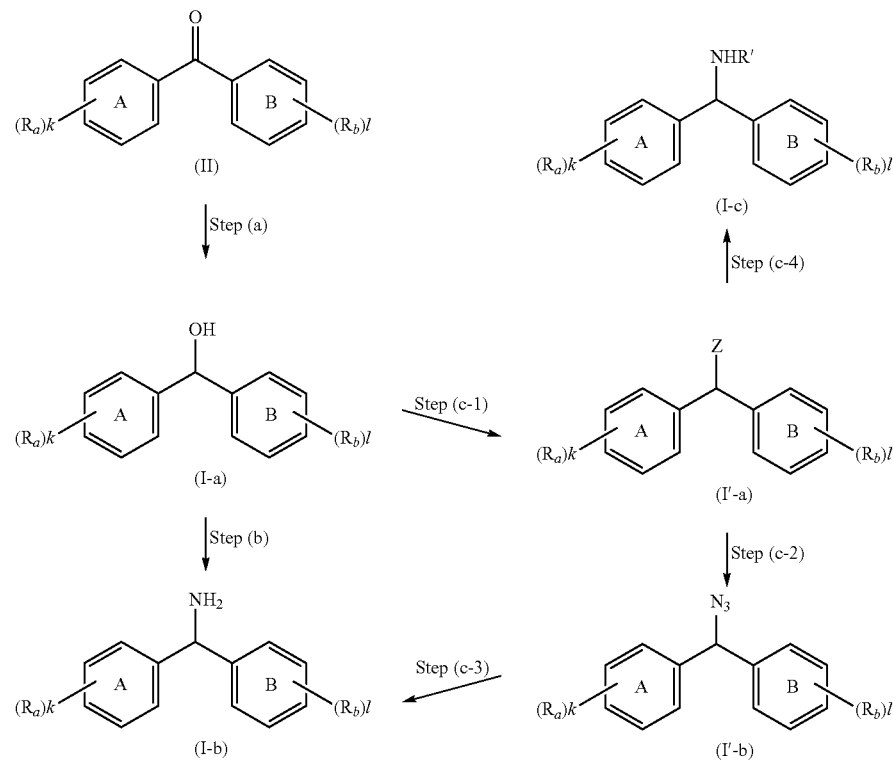

wherein the symbols are as defined above.

Step a

In this step, a compound represented by the formula (I-a), which is a compound of the present invention wherein Y is a hydroxyl group, (hereinafter to be abbreviated as compound (I-a)) is produced by reducing a compound represented by the formula (II) (hereinafter to be abbreviated as compound (II)).

The reduction reaction can be performed by a method using a reducing agent or a catalytic hydrogenation reaction.

The method using a reducing agent is generally performed is in a solvent that does not influence the reaction.

Examples of the reducing agent include metal hydride (sodium borohydride, lithium borohydride, sodium cyanoborohydride, sodium triacetoxyborohydride, dibutylaluminum hydride, aluminum hydride, lithium aluminum hydride etc.) and the like. Of these, sodium borohydride, dibutylaluminum hydride and the like are preferable.

The amount of the reducing agent to be used is generally 0.5-5 mol, preferably 1-3 mol, per 1 mol of compound (II).

The reaction is generally performed in a solvent that does not influence the reaction. Examples of the solvent include alcohols such as methanol, ethanol and the like; halogenated hydrocarbons such as chloroform, dichloromethane and the like; ethers such as diethyl ether, tetrahydrofuran, dioxane and the like; aromatic hydrocarbons such as toluene, xylene and the like; amides such as N,N-dimethylformamide etc. and the like or a mixture thereof. Of these, tetrahydrofuran, toluene, methanol, chloroform and the like are preferable.

The reaction temperature is generally 0-100° C., preferably 30-70° C., and the reaction time is generally 1-24 hr, preferably 2-5 hr.

The catalytic hydrogenation reaction is generally performed under a hydrogen atmosphere in the presence of catalyst in a solvent that does not influence the reaction.

Examples of the catalyst include palladiums such as palladium carbon, palladium hydroxide, palladium oxide and the like; nickels such as Raney-nickel etc. and the like. Of these, palladium carbon and the like are preferable.

The amount of the catalyst to be used is generally 5%-30% by mass, preferably 5-20 mass %, relative to compound (II).

Examples of the solvent include alcohols such as methanol, ethanol and the like; halogenated hydrocarbons such as chloroform, dichloromethane and the like; ethers such as diethyl ether, tetrahydrofuran, dioxane and the like; aromatic hydrocarbons such as toluene, xylene and the like; amides such as N,N-dimethylformamide and the like or a mixture thereof. Of these, methanol, tetrahydrofuran and the like are preferable.

The hydrogen pressure under which the reaction is performed is generally 1-5 atm, preferably 1-3 atm.

The reaction temperature is generally 20-80° C., preferably 30-50° C., and the reaction time is generally 1-30 hr, preferably 2-8 hr.

Step b

In this step, compound (I-a) is reacted with a compound having a —$CONH_2$ group or a —$OCONH_2$ group, and treated with a base to produce the compound of the present invention wherein Y is an amino group, which is represented by the formula (I-b) (hereinafter to be abbreviated as compound (I-b)).

The reaction with compound (I-a) and a compound having a —$CONH_2$ group or a —$OCONH_2$ group is generally performed with an acid catalyst in a solvent that does not influence the reaction, by reacting compound (I-a) with a compound having a —$CONH_2$ group or a —$OCONH_2$ group.

Examples of the acid catalyst include methanesulfonic acid, trifluoromethanesulfonic acid, p-toluenesulfonic acid and the like. Of these, methanesulfonic acid, toluenesulfonic acid and the like are preferable.

The amount of the acid catalyst to be used is generally 0.05-0.5 mol, preferably 0.1-0.3 mol, per 1 mol of compound (I-a).

Examples of the compound having a —$CONH_2$ group or a —$OCONH_2$ group include Fmoc-$NH_2$, $HCONH_2$, $CF_3CONH_2$, Ac$NH_2$, EtO$CONH_2$, Cbz-$NH_2$ and the like. Of these, EtO$CONH_2$, Fmoc-$NH_2$, Cbz-$NH_2$ and the like are preferable. Here, the "Fmoc-" means a 9-fluorenylmethoxycarbonyl group, and the "Cbz-" means a benzyloxycarbonyl group.

The amount of the compound to be used is generally 1-10 mol, preferably 1-5 mol, per 1 mol of compound (I-a).

Examples of the solvent include aromatic hydrocarbons such as toluene, xylene and the like; ethers such as diethyl ether, tetrahydrofuran, dioxane and the like; halogenated hydrocarbons such as chloroform, dichloromethane etc. and the like or a mixture thereof. Of these, toluene, tetrahydrofuran and the like are preferable.

The reaction temperature is generally 60-150° C., preferably 70-110° C., reaction time is generally 1-30 hr, preferably 2-6 hr.

Then, the obtained compound is treated with a base. The reaction is generally performed in a solvent that does not influence the reaction.

Examples of the base include dimethylamine, diethylamine, piperidine, morpholine, 1,8-diazabicyclo[5.4.0]-7-undecene and the like. Of these, diethylamine, 1,8-diazabicyclo[5.4.0]-7-undecene and the like are preferable.

The amount of the base to be used is generally 2-50 mol, preferably 5-30 mol, per 1 mol of compound (I-a).

Examples of the solvent include halogenated hydrocarbons such as chloroform, dichloromethane and the like; aromatic hydrocarbons such as toluene, xylene and the like; ethers such as tetrahydrofuran, dioxane and the like; nitriles such as acetonitrile and the like; and a mixture thereof. Of these, chloroform, tetrahydrofuran, dichloromethane, acetonitrile and the like are preferable.

The reaction temperature is generally 10-80° C., preferably 20-50° C., and the reaction time is generally 1-30 hr, preferably 1-5 hr.

Compound (I-b) can also be produced from step (c-1) to step (c-3).

Step (c-1)

In this step, compound (I-a) is chlorinated or brominated to produce a compound represented by the formula (I'-a) (hereinafter to be abbreviated as compound (I'-a)).

The reaction is generally performed in a solvent that does not influence the reaction, by reacting compound (I-a) with a chlorinating agent or a brominating agent.

Examples of the chlorinating agent include acetyl chloride and thionyl chloride. Examples of the brominating agent include acetyl bromide, phosphorus tribromide, diphenylphosphine/bromine and the like.

The amount of the chlorinating agent or brominating agent to be used is generally 0.8-10 equivalents, preferably 1-5 equivalents, relative to compound (I-a).

Examples of the solvent include halogenated hydrocarbons such as chloroform, dichloromethane and the like; aromatic hydrocarbons such as toluene, xylene and the like; ethers such as tetrahydrofuran, dioxane and the like; and a mixture thereof. Of these, chloroform, tetrahydrofuran, toluene and the like are preferable.

The reaction temperature is generally 10-150° C., preferably 30-80° C., and the reaction time is generally 0.5-30 hr, preferably 2-20 hr.

Step (c-2)

In this step, compound (I'-a) is azidated to produce a compound represented by the formula (I'-b) (hereinafter to be abbreviated as compound (I'-b)).

The reaction is generally performed in a solvent that does not influence the reaction, by reacting compound (I'-a) with an azidating agent.

Example of the azidating agent includes sodium azide.

The amount of the azidating agent to be used is generally 1-10 mol, preferably 1-5 mol, per 1 mol of compound (I'-a).

Examples of the solvent include halogenated hydrocarbons such as chloroform, dichloromethane and the like; aromatic hydrocarbons such as toluene, xylene and the like; ethers such as tetrahydrofuran, dioxane and the like; amides such as N,N-dimethylformamide and the like; and a mixture thereof. Of these, chloroform, N,N-dimethylformamide and the like are preferable.

The reaction temperature is generally 10-150° C., preferably 20-100° C., and the reaction time is generally 0.5-30 hr, preferably 2-20 hr.

Step (c-3)

In this step, compound (I'-b) is aminated to produce compound (I-b).

The reaction is generally performed in the presence of water in a solvent that does not influence the reaction, by reacting compound (I'-b) with triphenylphosphine.

The amount of triphenylphosphine to be used is generally 1-10 mol, preferably 1-5 mol, per 1 mol of compound (I'-b).

The amount of water to be used is generally 1-10 mol, preferably 1-5 mol, per 1 mol of compound (I'-b).

Examples of the solvent include aromatic hydrocarbons such as toluene, xylene and the like; ethers such as tetrahydrofuran, dioxane and the like; and a mixture thereof. Of these, toluene, tetrahydrofuran and the like are preferable.

The reaction temperature is generally 10-150° C., preferably 20-100° C., and the reaction time is generally 0.5-30 hr, preferably 2-20 hr.

Step (c-4)

In this step, compound (I'-a) is reacted with a compound having an NHR' group (R' is an alkyl group or an aralkyl group) to give the compound of the present invention wherein Y is a —NHR' group, which is represented by the formula (I-c) (hereinafter to be abbreviated as compound (I-c)).

The reaction is generally performed in the presence of a base, where necessary, in a solvent that does not influence the reaction, by reacting compound (I'-a) with amine represented by R'—NH$_2$.

The amount of amine to be used is generally 1-10 mol, preferably 2-5 mol, per 1 mol of compound (I'-a).

Examples of the base include tertiary amine such as triethylamine, diisopropylethylamine and the like, and the like. Of these, triethylamine, diisopropylethylamine and the like are preferable.

The amount of the base to be used is generally 1-2 mol, preferably 1-1.5 mol, per 1 mol of compound (I'-a).

Examples of the solvent include aromatic hydrocarbons such as toluene, xylene and the like; ethers such as tetrahydrofuran, dioxane and the like; and, halogen solvents such as chloroform, dichloromethane and the like and a mixture thereof. Of these, toluene, tetrahydrofuran, chloroform and the like are preferable.

The reaction temperature is generally 10-100° C., preferably 20-60° C., and the reaction time is generally 0.5-30 hr, preferably 2-20 hr.

Compound (II) used as the starting compound wherein the "organic group having an aliphatic hydrocarbon group" is bonded to ring A and/or ring B via —O— can be produced, for example, by the following method.

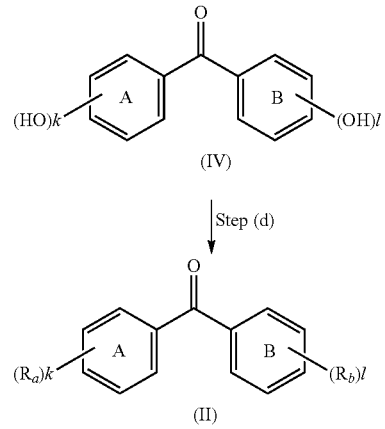

wherein each group is as defined above.

Step d

In this step, group $R_a$ and/or group $R_b$ is/are introduced into the hydroxyl group of a compound represented by the formula (IV) (hereinafter to be abbreviated as compound (IV)) to produce compound (II).

The reaction is generally performed in the presence of a base in a solvent that does not influence the reaction, using halide corresponding to group $R_a$ and/or group $R_b$.

Examples of the halide corresponding to group $R_a$ and/or group $R_b$ include corresponding chloride, corresponding bromide and corresponding iodide. Of these, corresponding bromide and corresponding iodide are preferable.

The amount of the halide to be used is appropriately determined according to the number of hydroxyl groups in compound (IV). It is generally 0.8-2 equivalents, preferably 1-1.5 equivalents, relative to the hydroxyl group.

Examples of the base include alkali metal salts such as is sodium carbonate, sodium hydrogen carbonate, potassium carbonate, sodium hydride, potassium hydride, potassium butoxide and the like; amines such as pyridine, triethylamine, N,N-dimethylaniline, 1,8-diazabicyclo[5.4.0]-7-undecene and the like; and the like. Of these, sodium carbonate, potassium carbonate, sodium hydride and the like are preferable.

The amount of the base to be used is generally 0.8-3 mol, preferably 1-2 mol, per 1 mol of compound (IV).

Examples of the solvent include aromatic hydrocarbons such as toluene, xylene and the like; ethers such as diethyl ether, tetrahydrofuran, dioxane and the like; amides such as dimethylformamide, dimethylacetamide and the like; halogenated hydrocarbons such as chloroform, dichloromethane and the like; nitriles such as acetonitrile and the like, etc. and a mixture thereof. Of these, dimethylformamide, tetrahydrofuran, toluene, N-methylpyrrolidone and the like are preferable.

The reaction temperature is generally 50-150° C., preferably 60-120° C., and the reaction time is generally 2-30 hr, preferably 3-10 hr.

Compound (II) wherein the organic group having an aliphatic hydrocarbon group is bonded to ring A and/or ring B not via —O— can also be produced according to the above-mentioned method, or an appropriate modification of the above-mentioned method. Such modification can be performed by using reactions generally employed in the field. For example, when the "organic group having an aliphatic hydrocarbon group" is bonded to ring A and/or ring B via —CONH—, compound (IV) having a carboxyl group and amine compound(s) corresponding to group $R_a$ and/or group $R_b$ are subjected to a dehydrating condensation.

3. Organic Synthesis Reaction Method

The compound of the present invention can be used as a protecting reagent (anchor) for various organic synthesis reactions. For example, the following steps are performed.
(i) a step of dissolving the compound of the present invention in soluble solvent (dissolution step)
(ii) a step of bonding the compound of the present invention dissolved in soluble solvent as obtained in the above-mentioned step to a reactive substrate (bonding step)
(iii) a step of precipitating the bonded product obtained in the above-mentioned step (precipitation step).

Step i (Dissolution Step)

In this step, the compound of the present invention is dissolved in a soluble solvent.

As the solvent, a general organic solvent can be used. Since superior reactivity can be expected when the solubility in the solvent is higher, a solvent in which the compound of the present invention shows high solubility is preferably selected. Specifically, halogenated hydrocarbon such as chloroform, dichloromethane and the like; and a nonpolar organic solvent such as 1,4-dioxane, tetrahydrofuran and the like can be mentioned. These solvents may be used in a mixture of two or more kinds at an appropriate ratio. In addition, the above-mentioned halogenated hydrocarbons and nonpolar organic solvent may be mixed with aromatic hydrocarbon such as benzene, toluene, xylene and the like; nitrile such as acetonitrile, propionitrile and the like; ketone such as acetone, 2-butanone and the like; amide such as N,N-dimethylformamide and the like; sulfoxide such as dimethyl sulfoxide and the like at an appropriate ratio and used as long as the compound of the present invention is dissolved.

Step ii (Bonding Step)

In this step, the compound of the present invention dissolved in a soluble solvent, which is obtained in the above-mentioned step, is bonded to a reactive substrate.

As to the reactive substrate, when the compound of the present invention wherein Y is a hydroxyl group is used as an anchor, the reactive substrate is a compound having a —CONHR group, and when the compound of the present invention wherein Y is a —NHR group is used as an anchor, the reactive substrate is a compound having a —COOH group.

The amount of the reactive substrate to be used is generally 1-10 mol, preferably 1-5 mol, per 1 mol of the compound of the present invention.

When Y is a hydroxyl group, the compound of the present invention is generally reacted with a reactive substrate using an acid catalyst in a solvent that does not influence the reaction.

Examples of the acid catalyst include methanesulfonic acid, trifluoromethanesulfonic acid, p-toluenesulfonic acid and the like. Of these, methanesulfonic acid, toluenesulfonic acid and the like are preferable.

The amount of the acid catalyst to be used is generally 0.05-0.5 mol, preferably 0.1-0.3 mol, per 1 mol of the compound of the present invention.

Examples of the solvent include aromatic hydrocarbons such as toluene, xylene and the like; ethers such as diethyl ether, tetrahydrofuran, dioxane and the like; halogenated hydrocarbons such as chloroform, dichloromethane and the like, etc. and a mixture thereof. Of these, toluene, tetrahydrofuran and the like are preferable.

The reaction temperature is generally 50° C.-150° C., preferably 60° C.-120° C., and the reaction time is generally 1-30 hr.

When Y is a —NHR group, the compound of the present invention is generally condensed with a reactive substrate using a condensing agent in a solvent that does not influence the reaction.

Examples of the condensing agent include dicyclohexylcarbodiimide (DCC), diisopropylcarbodiimide (DIC), N-ethyl-N'-3-dimethylaminopropylcarbodiimide and hydrochloride thereof (EDC HCl), hexafluorophosphoric acid (benzotriazol-1-yloxy)tripyrrolizinophosphonium (PyBop), O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluoroborate (HBTU) and the like.

The amount of the condensing agent to be used is generally 1-10 mol, preferably 1-5 mol, per 1 mol of the compound of the present invention.

Where necessary, the condensing agent may be used along with a promoter such as N-hydroxysuccinimide, 1-hydroxybenzotriazole (HOBt) and the like.

The amount of the promoter to be used is generally 0.1-2 mol, preferably 0.1-1.5 mol, per 1 mol of the compound of the present invention.

Examples of the solvent include halogenated hydrocarbons such as chloroform, dichloromethane and the like; aromatic hydrocarbons such as toluene, xylene and the like; ethers such as diethyl ether, tetrahydrofuran, dioxane and the like; etc. and a mixture thereof. Of these, chloroform, tetrahydrofuran, dichloromethane and the like are preferable.

The reaction temperature is generally 0-50° C., preferably 10-30° C., and the reaction time is generally 1-30 hr, preferably 2-5 hr.

For confirmation of the progress of the reaction, a method similar to general liquid phase organic synthesis reaction can be applied. That is, thin layer silica gel chromatography, high performance liquid chromatography and the like can be used to track the reaction.

Step iii (Precipitation Step)

In this step, the solvent used to dissolve the bonded product obtained in the above-mentioned step is changed (e.g., change of solvent composition, change of solvent kind) to cause precipitation to isolate the bonded product. That is, the reaction is performed under the conditions where the bonded product is dissolved and, after the reaction, the solvent is evaporated, and then substituted to allow precipitation of the bonded product and remove impurities. As the substitution solvent, polar organic solvents such as methanol, acetonitrile and the like are used.

Step iv (Removal Step)

After a desired reaction of the bonded product isolated by precipitation, the anchor derived from the compound of the present invention is finally removed (removal step).

The anchor to be removed here is a group represented by the formula (I-d):

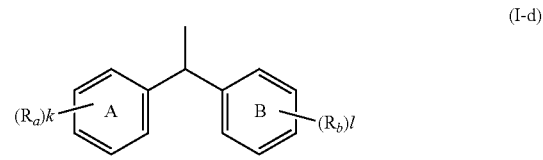

(I-d)

wherein each group is as defined above.

That is, when Y is a hydroxyl group, the —CONHR group of the reactive substrate is the same as the final —CONHR group, but when Y is a —NHR group, the —COOH group of the reactive substrate is finally converted to a —CONHR.

The anchor is removed by a treatment with acid and the like. Examples of the acid include trifluoroacetic acid (TFA), hydrochloric acid, sulfuric acid, methanesulfonic acid, p-toluenesulfonic acid and the like. Of these, trifluoroacetic acid is preferable.

The amount of the acid to be used is generally 3-100 mol, preferably 5-50 mol, per 1 mol of the bonded product.

The reaction temperature is generally 0° C.-80° C., preferably 10° C.-50° C. The reaction time is generally 0.5-24 hr.

Utilizing the above-mentioned steps, peptide can be synthesized in a liquid phase. By the liquid phase synthesis of peptide, a peptide finally having C-terminal etc., which are of a carboxamide type, can be produced. The detail is explained below.

(1) a step of condensing the compound of the present invention wherein Y is a hydroxyl group with N-protected amino acid or N-protected peptide having a —CONHR group, or condensing the compound of the present invention wherein Y is —NHR group with N-protected amino acid or N-protected peptide having a —COOH group to give C-diphenylmethane-protected amino acid or C-diphenylmethane-protected peptide (C-terminal etc. protection step with diphenylmethane)
(2) a step of deprotecting the N-terminal of the amino acid or peptide obtained in the above-mentioned step (N-terminal deprotection step),
(3) a step of condensing the N-terminal of the amino acid or peptide obtained in the above-mentioned step with N-protected amino acid or N-protected peptide (peptide chain elongation step), and
(4) a step of precipitating the peptide obtained in the above-mentioned step (precipitation step).

Step 1 (C-Terminal Etc. Protection Step with Diphenylmethane)

In this step, the diphenylmethane compound of the present invention is condensed with the C-terminal of N-protected amino acid or N-protected peptide to give C-diphenylmethane-protected amino acid or C-diphenylmethane-protected peptide.

N-protected amino acid or N-protected peptide having a —CONHR group, and N-protected amino acid or N-protected peptide having a —COOH group at the C-terminal etc. may be commercially available product, or may be produced by a method conventionally known in the peptide field.

When Y is a hydroxyl group, the condensation reaction of the compound of the present invention and N-protected amino acid or N-protected peptide having a —CONHR group at the C-terminal etc. is generally performed using an acid catalyst in a solvent that does not influence the reaction.

The amount of the amino acid or peptide to be used is generally 1-10 mol, preferably 1-5 mol, per 1 mol of the compound of the present invention.

Examples of the acid catalyst include methanesulfonic acid, p-toluenesulfonic acid and the like. Of these, methanesulfonic acid, toluenesulfonic acid and the like are preferable.

The amount of the acid catalyst to be used is generally 0.05-0.5 mol, preferably 0.1-0.3 mol, per 1 mol of the compound of the present invention.

Examples of the solvent include aromatic hydrocarbons such as toluene, xylene and the like; ethers such as diethyl ether, tetrahydrofuran, dioxane and the like; halogenated hydrocarbons such as chloroform, dichloromethane and the like etc. and a mixture thereof. Of these, toluene, tetrahydrofuran and the like are preferable.

The reaction temperature is generally 60-150° C., preferably 70-110° C., and the reaction time is generally 1-30 hr, preferably 2-6 hr.

When Y is a —NHR group, the condensation reaction of the compound of the present invention and N-protected amino acid or N-protected peptide having a —COOH group is generally performed using a condensing agent in a solvent that does not influence the reaction.

The amount of the amino acid or peptide to be used is generally 1-10 mol, preferably 1-5 mol, per 1 mol of the compound of the present invention.

Examples of the condensing agent include dicyclohexylcarbodiimide (DCC), diisopropylcarbodiimide (DIC), N-ethyl-N'-3-dimethylaminopropylcarbodiimide and hydrochloride thereof (EDC HCl), hexafluorophosphoric acid (benzotriazol-1-yloxy)tripyrrolizinophosphonium (PyBop), O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluoroborate (HBTU) and the like.

The amount of the condensing agent to be used is generally 1-10 mol, preferably 1-5 mol, per 1 mol of the compound of the present invention.

Where necessary, the condensing agent may be used along with a promoter such as N-hydroxysuccinimide, 1-hydroxybenzotriazole (HOBt) and the like.

The amount of the promoter to be used is generally 0.1-2 mol, preferably 0.1-1.5 mol, per 1 mol of the compound of the present invention.

Examples of the solvent include halogenated hydrocarbons such as chloroform, dichloromethane and the like; aromatic hydrocarbons such as toluene, xylene and the like; ethers such as diethyl ether, tetrahydrofuran, dioxane and the like etc. and a mixture thereof. Of these, chloroform, tetrahydrofuran, dichloromethane and the like are preferable.

The reaction temperature is generally 0-50° C., preferably 10-30° C., and the reaction time is generally 1-30 hr, preferably 2-5 hr.

Alternatively, a —COOH group of N-protected amino acid or N-protected peptide having a —COOH group may be activated in the presence of a base in a solvent that does not influence the reaction, and then it is reacted with the compound of the present invention.

The amount of the amino acid or peptide to be used is generally 1-10 mol, preferably 1-5 mol, per 1 mol of the compound of the present invention.

Examples of the activator of the —COOH group include chlorocarbonates such as ethyl chlorocarbonate, isobutyl chlorocarbonate and the like and the like.

The amount of the activator of the —COOH group to be used is generally 0.8-2 mol, preferably 1-1.5 mol, per 1 mol of the N-protected amino acid or N-protected peptide.

Examples of the base include tertiary amines such as triethylamine, diisopropylethylamine and the like, and the like. Of these, triethylamine, diisopropylethylamine and the like are preferable.

The amount of the base to be used is generally 1-2 mol, preferably 1-1.5 mol, per 1 mol of the amino acid or peptide.

Examples of the solvent include ethers such as diethyl ether, tetrahydrofuran, dioxane and the like; halogenated hydrocarbons such as chloroform, dichloromethane and the like; aromatic hydrocarbons such as toluene, xylene and the like, etc. and a mixture thereof. Of these, chloroform, dichloromethane, tetrahydrofuran and the like are preferable.

The reaction temperature is generally −10-30° C., preferably 10-30° C., and the reaction time is generally 1-30 hr, preferably 2-5 hr.

Step 2 (N-Terminal Deprotection Step)

In this step, the N-terminal of the C-diphenylmethane-protected amino acid or C-diphenylmethane-protected peptide obtained in step 1 is removed.

Deprotection is appropriately selected according to the kind of the N-protecting group. A group that can be removed under conditions different from those for the removal of the anchor (the group represented by the formula (I-d)) derived from the compound of the present invention is preferable. For example, an Fmoc group is removed by treating with a base. The reaction is generally performed in a solvent that does not influence the reaction.

Examples of the base include dimethylamine, diethylamine, morpholine, piperidine, 1,8-diazabicyclo[5.4.0]-7-undecene and the like. Of these, diethylamine, 1,8-diazabicyclo[5.4.0]-7-undecene and the like are preferable.

The amount of the base to be used is generally 2-100 mol, preferably 5-30 mol, per 1 mol of the amino acid or peptide.

Examples of the solvent include halogenated hydrocarbons such as chloroform, dichloromethane and the like; aromatic hydrocarbons such as toluene, xylene and the like; ethers such as diethyl ether, tetrahydrofuran, dioxane and the like; nitriles such as acetonitrile and the like, and a mixture thereof. Of these, chloroform, dichloromethane, tetrahydrofuran and the like are preferable.

The reaction temperature is generally 10-50° C., preferably 20-40° C., and the reaction time is generally 1-30 hr, preferably 2-10 hr.

Step 3 (Peptide Chain Elongation Step)

In this step, the N-terminal of amino acid or peptide deprotected in N-terminal in step 2 is condensed with N-protected amino acid or N-protected peptide.

This step is performed according to the method of the above-mentioned step 1 wherein Y is a —NHR group.

Step 4 (Precipitation Step)

This step is performed in the same manner as in the precipitation step in the above-mentioned step iii.

The N-protected peptide obtained in step 4 is subjected to a desired number of repeats of steps (5)-(7), and finally to a removal step in the same manner as in step iv to finally remove the anchor derived from the compound of the present invention.

(5) a step of deprotecting the N-terminal of the peptide obtained in the precipitation step,
(6) a step of condensing the N-terminal of peptide obtained in the above-mentioned step with N-protected amino acid or N-protected peptide, and
(7) a step of precipitating the peptide obtained in the above-mentioned step.

Step 5 (N-Terminal Deprotection Step)

This step is performed in the same manner as in the N-terminal deprotection step of step 2.

Step 6 (Peptide Chain Elongation Step)

This step is performed in the same manner as in the peptide chain elongation step of step 3.

Step 7 (Precipitation Step)

This step is performed in the same manner as in the precipitation step of step iii.

In each reaction, when the starting compound has a hydroxyl group, an amino group, a carboxy group or a carbonyl group (particularly when amino acid or peptide has a functional group in the side chain), a protecting group generally used in the peptide chemistry etc. may be introduced into these groups. The object compound can be obtained by removing the protecting group as necessary after the reaction.

Examples of the hydroxyl-protecting group include ($C_1$-$C_6$)alkyl group (e.g., methyl, ethyl, propyl, isopropyl, butyl, tert-butyl), phenyl group, trityl group, ($C_7$-$C_{10}$)aralkyl group (e.g., benzyl), formyl group, ($C_1$-$C_6$)alkyl-carbonyl group (e.g., acetyl, propionyl), benzoyl group, ($C_7$-$C_{10}$)aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_6$)alkyl group (e.g., methyl, ethyl, propyl), a ($C_1$-$C_6$)alkoxy group (e.g., methoxy, ethoxy, propoxy), a nitro group and the like.

Examples of the amino-protecting group include formyl group, ($C_1$-$C_6$)alkyl-carbonyl group (e.g., acetyl, propionyl), ($C_1$-$C_6$)alkoxy-carbonyl group (e.g., methoxycarbonyl, ethoxycarbonyl, tert-butoxycarbonyl), benzoyl group, ($C_7$-$C_{10}$) aralkyl-carbonyl group (e.g., benzylcarbonyl), ($C_7$-$C_{14}$) aralkyloxy-carbonyl group (e.g., benzyloxycarbonyl, 9-fluorenylmethoxycarbonyl), trityl group, phthaloyl group, N,N-dimethylaminomethylene group, silyl group (e.g., trimethylsilyl, triethylsilyl, dimethylphenylsilyl, tert-butyldimethylsilyl, tert-butyldiethylsilyl), ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_8$) alkoxy group (e.g., methoxy, ethoxy, propoxy), a nitro group and the like.

Examples of the carboxy-protecting group include ($C_1$-$C_6$) alkyl group (e.g., methyl, ethyl, propyl, isopropyl, butyl, tert-butyl), ($C_7$-$C_{10}$)aralkyl group (e.g., benzyl), phenyl group, trityl group, silyl group (e.g., trimethylsilyl, triethylsilyl, dimethylphenylsilyl, tert-butyldimethylsilyl, tert-butyldiethylsilyl, tert-butyldiphenylsilyl), ($C_2$-$C_6$)alkenyl group (e.g., 1-allyl) and the like can be mentioned. These groups is a halogen atom (e.g., fluorine, chlorine, bromine, iodine), a ($C_1$-$C_6$)alkoxy group (e.g., methoxy, ethoxy, propoxy), a nitro group and the like.

Examples of the carbonyl-protecting group include cyclic acetal (e.g., 1,3-dioxane), acyclic acetal (e.g., di-($C_1$-$C_6$) alkylacetal) and the like.

These protecting groups can be removed according to a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammoniumfluoride, palladium acetate, trialkylsilylhalide (e.g., trimethylsilyliodide, trimethylsilylbromide etc.) and the like, a reduction method and the like are used.

4. Kit for Liquid Phase Synthesis of Peptide

The present invention also provides a kit for liquid phase synthesis of peptide, which contains the above-mentioned compound of the present invention as an essential constituent component. The kit may contain, besides the compound of the present invention, other components necessary for liquid phase synthesis reaction of peptide, for example, various solvents used for the reaction, amino acid (or peptide) to be the starting material and the like. When desired, a manual of liquid phase synthesis of peptide using the compound of the present invention can also be attached.

EXAMPLES

The present invention is explained in more detail in the following by referring to Examples, which are not to be construed as limitative. The reagents, apparatuses and materials used in the present invention are commercially available unless otherwise specified. In the present specification, when amino acid and the like are indicated by abbreviation, each indication is based on the abbreviation of the IUPAC-IUB Commission on Biochemical Nomenclature or conventional abbreviations in the art.

For mass spectrometry, flow injection analysis (FIA) was performed using high-performance liquid chromatography/mass spectrometry device, LC-MSD (liquid chromatography) system 1100 Series (Agilent Technologies).

Ionization Mode: ESI
Ion Mode: Positive
Mass Spectrometry Part: quadrupole

Reference Example 1 alkylation of 2,3,4-trihydroxybenzophenone

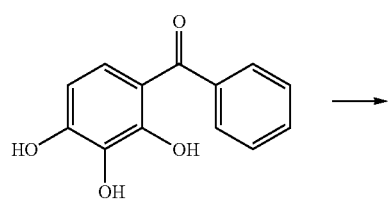

To 2,3,4-trihydroxybenzophenone (1.60 g, 6.95 mmol) was added DMF (30 ml), 1-bromooctadecane (7.3 g, 21.9 mmol) and potassium carbonate (4.32 g, 31.3 mmol), and the mixture was stirred at 80° C. overnight. The reaction mixture was cooled to room temperature, chloroform (100 ml) was added, and 1N hydrochloric acid (30 ml) was further added dropwise. After stirring, the mixture was partitioned, and the organic layer was washed with 1N hydrochloric acid (30 ml) and water (30 ml). The organic layer was evaporated under reduced pressure, and the residue was washed with methanol (30 ml). The obtained precipitate was slurry washed with methanol (45 ml) to give 2,3,4-trioctadecanoxybenzophenone (6.35 g, 6.43 mmol, yield 93%).

$^1$H-NMR (CDCl$_3$/300 MHz)

0.88 (9H, t, J=6.6, C$_{17}$H$_{34}$—C$\underline{H}_3$) 1.00-1.60 (92H, br, Alkyl-$\underline{H}$) 1.74 (2H, m, —O—CH$_2$—C$\underline{H}_2$—C$_{16}$H$_{33}$) 1.84 (2H, m, —O—CH$_2$—C$\underline{H}_2$—C$_{16}$H$_{33}$) 3.88 (2H, t, J=6.9, —O—C$\underline{H}_2$—C$_{17}$H$_{35}$) 4.00 (4H, m, —O—C$\underline{H}_2$—C$_{17}$H$_{35}$) 6.69 (1H, d, J=8.7, Ph C5-H) 7.12 (1H, d, J=8.7, Ph C6-H) 7.41 (2H, t, J=7.2, Ph C3',5'-H) 7.51 (1H, d, J=7.2, Ph C4'-H) 7.78 (1H, d, J=7.2, Ph C2',6'-H)

Example 1

Reduction of 2,3,4-trioctadecanoxybenzophenone

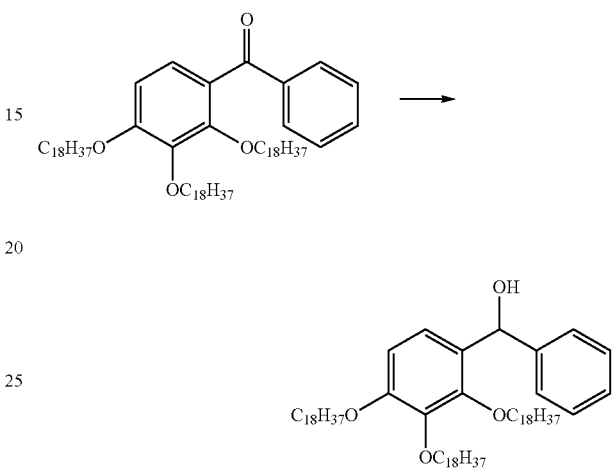

To 2,3,4-trioctadecanoxybenzophenone (3 g, 3.04 mmol) obtained in Reference Example 1 were added chloroform (30 ml), methanol (3 ml) and sodium borohydride (346 mg, 9.14 mmol), and the mixture was stirred at 45° C. overnight. The reaction mixture was cooled to room temperature and 1N hydrochloric acid (15 ml) was added dropwise. After stirring, the mixture was partitioned, and the organic layer was washed with water (15 ml×3). The organic layer was evaporated under reduced pressure, and acetonitrile (30 ml) was added to the residue. The precipitate was collected by filtration to give 2,3,4-trioctadecanoxybenzhydrol (2.91 g, 2.94 mmol, yield 97%).

$^1$H-NMR (CDCl$_3$/300 MHz)

0.88 (9H, t, J=6.6, C$_{17}$H$_{34}$—C$\underline{H}_3$) 1.10-1.65 (92H, br, Alkyl-$\underline{H}$) 1.65-1.90 (4H, m, —O—CH$_2$—C$\underline{H}_2$—C$_{16}$H$_{33}$) 3.03 (1H, br, s, —OH) 3.72 (1H, dt, J=6.6, 9.0, —O—C$\underline{H}_2$—C$_{17}$H$_{35}$) 3.95 (5H, m, —O—C$\underline{H}_2$—C$_{17}$H$_{35}$) 5.93 (1H, s, Ar—C$\underline{H}$OH-Ph) 6.59 (1H, d, J=8.7, Ph C5-H) 6.83 (1H, d, J=8.7, Ph C6-H) 7.20-7.41 (5H, m, Ph-$\underline{H}$)

Example 2

Fmoc Amination of 2,3,4-trioctadecanoxybenzhydrol

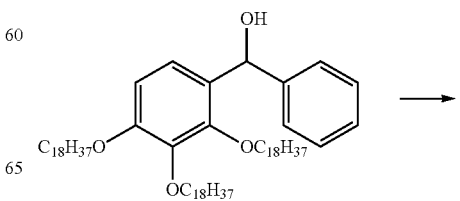

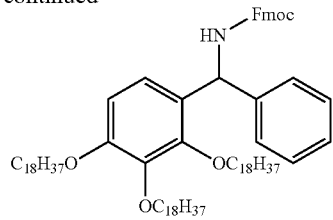

To 2,3,4-trioctadecanoxybenzhydrol (650 mg, 657 µmol) obtained in Example 1 were added toluene (10 ml) and Fmoc-NH$_2$ (189 mg, 790 µmol), and the mixture was warmed to 50° C. in an oil bath. Methanesulfonic acid (6.4 µl, 99 µmol) was added, and the mixture was heated to 100° C. and stirred for 6 hr. After confirmation of disappearance of a benzhydrol type anchor, the mixture was cooled to room temperature. Toluene (5 ml) and 5% aqueous sodium hydrogen carbonate (10 ml) were added and the mixture was stirred. After partitioning, the organic layer was further washed with water (10 ml×2). The organic layer was evaporated under reduced pressure, and the residue was washed with methanol (10 ml) to give N-Fmoc-[phenyl(2,3,4-trioctadecanoxyphenyl)methyl]amine (788 mg, yield 98%).

$^1$H-NMR (CDCl$_3$/300 MHz)

0.88 (9H, t, J=6.6, C$_{17}$H$_{34}$—C$\underline{H}_3$) 1.10-1.6592H, br, Alkyl-$\underline{H}$) 1.65-1.90 (4H, m, —O—CH$_2$—C$\underline{H}_2$—C$_{16}$H$_{33}$) 3.40-3.50 (1H, br, m, —O—C$\underline{H}_2$—C$_{17}$H$_{35}$) 3.95 (5H, br, s, —O—C$\underline{H}_2$—C$_{17}$H$_{35}$) 4.25 (1H, br, s, fluorene C9-$\underline{H}$) 4.40 (2H, br, m, fluorene-C$\underline{H}_2$—O) 5.85-5.95 (1H, br, Fmoc-N$\underline{H}$— or Fmoc-NH—C$\underline{H}$) 6.00-6.10 (1H, br, Fmoc-N$\underline{H}$— or Fmoc-NH—C$\underline{H}$) 6.61 (1H, br, d, J=8.7, Ph C5-H) 6.89 (1H, br, d, J=8.7, Ph C6-H) 7.10-7.50 (7H, br, m, Ph-$\underline{H}$, fluorene C2,7-$\underline{H}$) 7.55-7.65 (2H, br, fluorene C1,8-$\underline{H}$) 7.70-7.82 (2H, br, fluorene C4,5-H)

Example 3

Removal of Fmoc from N-Fmoc-[phenyl(2,3,4-trioctadecanoxyphenyl)methyl]amine

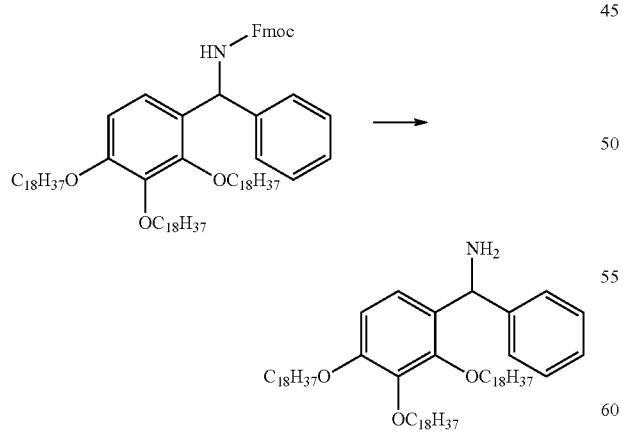

N-Fmoc-[phenyl (2,3,4-trioctadecanoxyphenyl)methyl]amine (830 mg, 684 µmol) obtained in Example 2 was dissolved in chloroform (10 ml) and acetonitrile (6 ml), diethylamine (2.04 ml, 1.97 mmol) was added dropwise and the mixture was stirred for 5 hr. The solvent was evaporated, and the residue was washed with acetonitrile (10 ml) to give [phenyl(2,3,4-trioctadecanoxyphenyl)methyl]amine (668 mg, 696 µmol, yield 99%).

$^1$H-NMR (CDCl$_3$/300 MHz)

0.88 (9H, t, J=6.6, C$_{17}$H$_{34}$—C$\underline{H}_3$) 1.10-1.65 (92H, br, Alkyl-$\underline{H}$) 1.65-1.90 (4H, m, —O—CH$_2$—C$\underline{H}_2$—C$_{16}$H$_{33}$) 3.75-3.89 (2H, m, —O—C$\underline{H}_2$—C$_{17}$H$_{35}$) 3.89-4.00 (4H, m, —O—C$\underline{H}_2$—C$_{17}$H$_{35}$) 5.40 (1H, s, Ar—C$\underline{H}$NH$_2$-Ph) 6.58 (1H, d, J=8.4, Ph C5-H) 6.89 (1H, d, J=8.4, Ph C6-H) 7.15-7.40 (5H, m, Ph-$\underline{H}$)

Example 4

Fmoc Amination of 4,4'-didocosoxybenzhydrol 4-1: synthesis of 4,4'-didocosoxy-benzophenone To 4,4'-dihydroxy-benzophenone (8.2 g, 38.3 mmol) and 1-bromodocosane (31.3 g, 80.4 mmol) were added DMF (300 mL) and potassium carbonate (15.9 g, 115 mmol) and the mixture was stirred at 80° C. for 6.5 hr. After confirmation of disappearance of monoalkylated form, the reaction mixture was ice-cooled and 1N hydrochloric acid (300 mL) and water (150 mL) were slowly added with sufficient stirring. The slurry was filtered, and the obtained crystals were washed with water and methanol to give 4,4'-didocosoxy-benzophenone (28.3 g, 34.1 mmol, 89%).

$^1$H-NMR (CDCl$_3$/300 MHz)

δ=0.88 (6H, t, J=6.6 Hz, OC$_{22}$H$_{45}$ C22-$\underline{H}$) 1.1-1.6 (76H, br, OC$_{22}$H$_{45}$ C3-21-$\underline{H}$) 1.81 (4H, m, OC$_{22}$H$_{45}$ C2-$\underline{H}$) 2.04 (1H, s, —O$\underline{H}$) 4.03 (4H, t, J=6.5 Hz, OC$_{22}$H$_{45}$ C1-$\underline{H}$) 6.94 (4H, d, J=8.8 Hz, Ph C3,3',5,5'-$\underline{H}$) 7.77 (4H, d, J=8.7 Hz, Ph C2,2',6,6'-$\underline{H}$)

4-2: synthesis of 4,4'-didocosoxybenzhydrol

To 4,4'-didocosoxy-benzophenone (28.3 g, 34.1 mmol) were added THF (300 mL) and methanol (15 mL) and the mixture was heated to 60° C. Sodium borohydride (6.10 g, 161 mmol) was added slowly, and the mixture was stirred at the same temperature for 4 hr. The reaction mixture was ice-cooled and 1N hydrochloric acid (80 mL) was added dropwise. THF was evaporated, water (450 mL) was added and 1N hydrochloric acid was added to pH 5-7. The slurry was filtered, and the obtained crystals were washed with water and methanol to give 4,4'-didocosoxybenzhydrol (28.5 g, 34.1 mmol, 99%).

$^1$H-NMR (CDCl$_3$/300 MHz)

δ=0.88 (6H, t, J=6.6 Hz, OC$_{22}$H$_{45}$ C22-$\underline{H}$) 1.1-1.6 (76H, br, OC$_{22}$H$_{45}$ C3-21-$\underline{H}$) 1.734H, m, OC$_{22}$H$_{45}$ C2-$\underline{H}$) 2.041H, s, —O$\underline{H}$) 3.93 (4H, t, J=6.6 Hz, OC$_{22}$H$_{45}$ C1-$\underline{H}$) 5.76 (1H, s, HO—C$\underline{H}$Ph$_2$) 6.85 (4H, d, J=8.7 Hz, Ph C3,3',5,5'-$\underline{H}$) 7.25 (4H, d, J=8.6 Hz, Ph C2,2',6,6'-$\underline{H}$)

4-3: Fmoc amination of 4,4'-didocosoxybenzhydrol

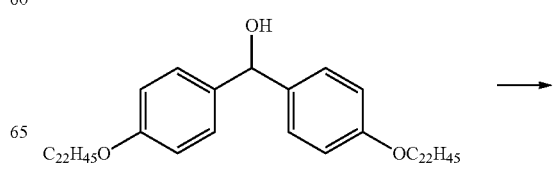

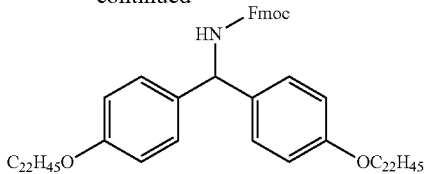

To 4,4'-didocosoxybenzhydrol (713 mg, 856 μmol) were added toluene (15 ml), Fmoc-NH$_2$ (246 mg, 1.03 mmol) and methanesulfonic acid (8.3 μl, 128 μmol), and the mixture was stirred at 100° C. for 3 hr. After confirmation of disappearance of a benzhydrol type anchor, the mixture was cooled to room temperature. 2.5% Aqueous sodium hydrogen carbonate (10 ml) was added and the mixture was stirred. After partitioning, the organic layer was further washed with water (10 ml×2). The organic layer was evaporated under reduced pressure, and the residue was washed with methanol (10 ml) to give N-Fmoc-di(4-docosoxyphenyl)methylamine (540 mg, 512 μmol, yield 60%).

$^1$H-NMR (CDCl$_3$/300 MHz)

0.88 (9H, t, J=6.6, C$_{21}$H$_{42}$—C$\underline{H}_3$) 1.10-1.50 82H, br, Alkyl-$\underline{H}$) 1.77 (4H, m, —O—CH$_2$—C$\underline{H}_2$—C$_{20}$H$_{41}$) 3.93 (4H, d, J=6.6, —O—C$\underline{H}_2$—C$_{21}$H$_{43}$) 4.21 (1H, br, s, fluorene C9-$\underline{H}$) 4.43 (2H, br, d, J=6.6, fluorene-C$\underline{H}_2$—O) 5.23 (1H, br, s, Fmoc-N$\underline{H}$— or Fmoc-NH—C$\underline{H}$) 5.85 (1H, br, s, Fmoc-N$\underline{H}$— or Fmoc-NH—C$\underline{H}$) 6.84 (4H, d, J=8.7, Ph C3,5-H) 7.11 (4H, d, J=8.7, Ph C2,6-H) 7.25-7.35 (2H, br, m, fluorene C2,7-$\underline{H}$) 7.39 (2H, br, t, J=6.9, fluorene C3,6-$\underline{H}$) 7.59 (2H, br, s, fluorene C1,8-$\underline{H}$) 7.75 (2H, br, d, J=6.6, fluorene C4,5-H)

Example 5

Removal of Fmoc from N-Fmoc-di(4-docosoxyphenyl)methylamine

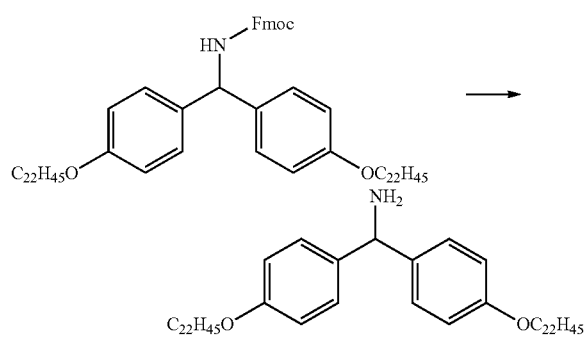

To dichloromethane (10 ml) was added DBU (1,8-diazabicyclo[5,4,0]-7-undecene, 200 μl), and N-Fmoc-di(4-docosoxyphenyl)methylamine (500 mg, 474 μmol) obtained in Example 4 was added and the mixture was stirred at room temperature for 5 hr. 1N Hydrochloric acid (1.3 ml) was added dropwise and, after stirring, the solvent was evaporated and the residue was washed with acetonitrile (10 ml) to give di(4-docosoxyphenyl)methylamine (340 mg, 408 μmol, yield 86%).

$^1$H-NMR (CDCl$_3$/300 MHz)

δ=0.88 (6H, t, J=6.6 Hz, OC$_{22}$H$_{45}$ C22-$\underline{H}$) 1.1-1.6 (78H, br, OC$_{22}$H$_{45}$ C3-21-$\underline{H}$, —NH$_2$) 1.75 (4H, m, OC$_{22}$H$_{45}$ C2-$\underline{H}$) 3.92 (4H, t, J=6.6 Hz, OC$_{22}$H$_{45}$ C1-$\underline{H}$) 5.12 (1H, s, H$_2$N—C$\underline{H}$Ph$_2$) 6.83 (4H, d, J=8.6 Hz, Ph C3,3',5,5'-$\underline{H}$) 7.24 (4H, d, J=8.6 Hz, Ph C2,2',6,6'-$\underline{H}$)

Example 6

Introduction of Fmoc-Gly-NH$_2$ into Benzhydrol Type Anchor

To a benzhydrol type anchor (4,4'-didocosoxyphenylbenzhydrol, hereinafter Dpm(OC$_{22}$)$_2$—OH, 1.0 g, 1.20 mmol) were added toluene (20 ml), Fmoc-Gly-NH$_2$ (533 mg, 1.80 mmol) and methanesulfonic acid (4.9 μl, 602 μmol), and the mixture was stirred at 90° C. for 1.5 hr. After confirmation of disappearance of benzhydrol type anchor, the mixture was cooled to room temperature, and 1.5% aqueous sodium hydrogen carbonate (10 ml) was added. The mixture was stirred and partitioned. The organic layer was washed with water (10 ml)×3, and evaporated under reduced pressure. The residue was precipitated with acetonitrile (15 ml) to give Fmoc-Gly-NH-Dpm(OC$_{22}$)$_2$ (1.32 g, yield 99% vs Dpm(OC$_{22}$)$_2$).

$^1$H-NMR (CDCl$_3$/300 MHz)

0.88 (9H, t, J=6.9, C$_{21}$H$_{42}$—C$\underline{H}_3$) 1.20-1.60 (82H, br, Alkyl-$\underline{H}$) 1.74 (4H, m, —O—CH$_2$—C$\underline{H}_2$—C$_{20}$H$_{41}$) 3.90 (6H, m, —O—C$\underline{H}_2$—C$_{21}$H$_{43}$, Fmoc-NH—C$\underline{H}_2$—COO—) 4.19 (1H, br, s, fluorene C9-$\underline{H}$) 4.41 (2H, d, J=6.9, fluorene-C$\underline{H}_2$—O) 5.38 (1H, br, s, Fmoc-N$\underline{H}$—) 6.13 (1H, d, J=7.8, Gly-N$\underline{H}$—CHAr$_2$ or Gly-NH—C$\underline{H}$Ar$_2$) 6.38 (1H, d, J=7.8, Gly-N$\underline{H}$—CHAr$_2$ or Gly-NH—C$\underline{H}$Ar$_2$) 6.81 (4H, d, J=8.4, Ph C3,5-H) 7.09 (4H, d, J=8.4, Ph C2,6-H) 7.25-7.33 (2H, br, m, Ph-$\underline{H}$, fluorene C2,7-$\underline{H}$) 7.39 (2H, t, J=7.5, fluorene C3,6-$\underline{H}$) 7.56 (2H, d, J=7.5, fluorene C1,8-$\underline{H}$) 7.75 (2H, d, J=7.5, fluorene C4,5-H)

Example 7

Removal of Fmoc from Fmoc-Gly-NH-Dpm(OC$_{22}$)$_2$ and Condensation of Fmoc-His(Trt)-OH Fmoc-Gly-NH-Dpm(OC$_{22}$)$_2$ (1.32 g) obtained in Example 6 was dissolved in chloroform-acetonitrile (3:1, 20 ml), and diethylamine (1.23 ml, 11.9 mmol) was added dropwise in an ice bath. The mixture was warmed to room temperature, and stirred for 1.5 hr. Diethylamine (1.23 ml, 11.9 mmol) was added and the mixture was stirred for 1.5 hr. Diethylamine (615 μl, 5.93 mmol) was added, and the mixture was stirred for 2 hr. Diethylamine (615 μl, 5.93 mmol) was added, and the mixture was further stirred for 1.5 hr. The solvent was evaporated, and the residue was precipitated with acetonitrile to give Gly-NH-Dpm as wet crystals. The obtained wet crystals were dissolved in chloroform (15 ml), Fmoc-His(Trt)-OH (811 mg, 1.31 mmol) and HOBt (18 mg, 0.131 mmol) were added at room temperature, EDC HCl (276 mg, 1.44 mmol) was added in an ice bath, and the mixture was stirred at room temperature overnight. The solvent was evaporated, and the residue was precipitated with methanol to give Fmoc-His(Trt)-Gly-NH-Dpm(OC$_{22}$)$_2$ (1.74 g, yield 97% vs Dpm-OH)).

Example 8

Removal of Fmoc from Fmoc-His(Trt)-Gly-NH-Dpm(OC$_{22}$)$_2$ and Condensation of Fmoc-Gln(Trt)-OH Fmoc-His(Trt)-Gly-NH-Dpm(OC$_{22}$)$_2$ (1.74 g) obtained in Example 7 was dissolved in chloroform-acetonitrile (3:1, 20 ml), and diethylamine (1.21 ml, 11.7 mmol) was added dropwise in an ice bath. The mixture was warmed to room temperature, and the mixture was stirred for 2 hr. Diethylamine (1.21 ml, 11.7 mmol) was added, and the mixture was further stirred for 2 hr. The solvent was evaporated, and the residue was precipitated with methanol. The obtained crystals were slurry washed with methanol and acetonitrile in this order to give wet crystals of His(Trt)-Gly-NH-Dpm(OC$_{22}$)$_2$. The obtained wet crystals were dissolved in chloroform (20 ml), Fmoc-Gln(Trt)-OH (785 mg, 1.29 mmol) and HOBt (17.4 mg, 129 mol) were added at room temperature, EDC HCl (271 mg, 1.41 mmol) was added in an ice bath, and the mixture was stirred at room temperature overnight. The solvent was evaporated, and the residue was precipitated with methanol to give Fmoc-Gln(Trt)-His(Trt)-Gly-NH-Dpm (OC$_{22}$)$_2$ (2.07 g, yield 93% vs Dpm(OC$_{22}$)$_2$—OH).

Example 9

Removal of Fmoc from Fmoc-Gln(Trt)-His(Trt)-Gly-NH-Dpm(OC$_{22}$)$_2$ and Condensation of Fmoc-Arg (Pbf)-OH Fmoc-Gln(Trt)-His(Trt)-Gly-NH-Dpm(OC$_{22}$)$_2$ (2.07 g) obtained in Example 8 was dissolved in chloroform-acetonitrile (2:1, 30 ml), and diethylamine (1.15 ml, 11.7 mmol) was added dropwise in an ice bath. The mixture was warmed to room temperature, and the mixture was stirred for 1.5 hr. Diethylamine (1.15 ml, 11.1 mmol) was added, and the mixture was further stirred for 2 hr. Diethylamine (575 µl, 5.54 mmol) was added, and the mixture was stirred for 1.5 hr. The solvent was evaporated, and the residue was precipitated with acetonitrile to give wet crystals of Gln(Trt)-His(Trt)-Gly-NH-Dpm(OC$_{22}$)$_2$. The obtained wet crystals were dissolved in chloroform (20 ml), Fmoc-Arg(Pbf)-OH (795 mg, 1.23 mmol) and HOBt (17 mg, 123 µmol) were added at room temperature, EDC HCl (258 mg, 1.35 mmol) was added in an ice bath, and the mixture was stirred at room temperature overnight. The solvent was evaporated, and the residue was precipitated with methanol to give Fmoc-Arg(Pbf)-Gln(Trt)-His (Trt)-Gly-NH-Dpm(OC$_{22}$)$_2$ (2.28 g, yield 84% vs Dpm (OC$_{22}$)$_2$—OH).
ESI-MS: Calcd 2270.4 [M+H]$^+$, 1135.7 [(M+2H)/2]$^+$. Found 2270.1 [M+H]$^+$, 1135.4 [(M+2H)/2]$^+$.

Example 10

Introduction of Fmoc-Gly-NH$_2$ into Benzhydrol Type Anchor

To a benzhydrol type anchor (2,3,4-trioctadecanoxybenzhydrol, hereinafter Bp-OH, 500 mg, 522 µmol) were added toluene (15 ml) and Fmoc-Gly-NH$_2$ (225 mg, 759 µmol), and the mixture was warmed to 50° C. in an oil bath. Methanesulfonic acid (4.9 µl, 76 µmol) was added, and the mixture was warmed to 100° C. and the mixture was stirred overnight. After confirmation of disappearance of a benzhydrol type anchor, and the mixture was cooled to room temperature, toluene (10 ml) and 1% aqueous sodium hydrogen carbonate (20 ml) were added, and the mixture was vigorously stirred for a short time. The aqueous layer containing the precipitated crystals was collected in a different container. The organic layer was washed with water (20 ml)×2, and respective aqueous layers were collected and extracted with chloroform (10 ml). The organic layer was evaporated under reduced pressure, and the residue was precipitated with methanol (10 ml) to give Fmoc-Gly-NH-Bp (633 mg, yield 99% vs Bp-OH).

$^1$H-NMR (CDCl$_3$/300 MHz)
0.88 (9H, t, J=6.9, C$_{17}$H$_{34}$—CH$_3$) 1.00-1.60 (92H, br, Alkyl-H) 1.70 (2H, m, —O—CH$_2$—CH$_2$—C$_{16}$H$_{33}$) 1.81 (2H, m, —O—CH$_2$—CH$_2$—C$_{16}$H$_{33}$) 3.24 (1H, m, —O—CH$_2$—C$_{17}$H$_{35}$) 3.80-4.10 (7H, m, —O—CH$_2$—C$_{17}$H$_{35}$, Fmoc-NH—CH$_2$—COO—) 4.22 (1H, br, s, fluorene C9-H) 4.39 (2H, d, J=6.6, fluorene-CH$_2$—O) 5.48 (1H, br, s, Fmoc-NH—) 6.31 (1H, br, d, J=8.7, Gly-NH—CHAr2 or Gly-NH—CHAr2) 6.60 (1H, d, J=8.4, Ph C5-H) 6.91 (1H, d, J=8.4, Ph C6-H) 7.00-7.35 (7H, br, m, Ph-H, fluorene C2,7-H) 7.39 (2H, t, J=7.5, fluorene C3,6-H) 7.59 (2H, d, J=7.5, fluorene C1,8-H) 7.76 (2H, d, J=7.5, fluorene C4,5-H)

Example 11

Removal of Fmoc from Fmoc-Gly-NH-Bp and Condensation of Fmoc-His(Trt)-OH

Fmoc-Gly-NH-Bp (666 mg) obtained in Example 10 was dissolved in chloroform (5 ml), and diethylamine (817 µl, 7.88 mmol) was added dropwise in an ice bath. The mixture was warmed to room temperature, acetonitrile (3 ml) was added and the mixture was stirred for 3 hr. Diethylamine (272 µl, 2.62 mmol) was added, and the mixture was further stirred for 1 hr. The solvent was evaporated, and the residue was precipitated with acetonitrile to give wet crystals of Gly-NH-Bp. The obtained wet crystals were dissolved in chloroform (10 ml), and Fmoc-His(Trt)-OH (358 mg, 578 µmol) and HOBt (7.80 mg, 57.7 µmol) were added at room temperature, and EDC.HCl (122 mg, 636 µmol) was added in an ice bath. The mixture was warmed to room temperature, and stirred overnight. After stirring, Fmoc-His(Trt)-OH (35.8 mg, 57.8 µmol) and EDC.HCl (12.2 mg, 63.6 µmol) were added, and the mixture was further stirred for 1.5 hr. The solvent was evaporated, and the residue was precipitated with methanol to give Fmoc-His(Trt)-Gly-NH-Bp (851 mg, yield 98% vs Bp-OH)).

Example 12

Removal of Fmoc from Fmoc-his(Trt)-Gly-NH-Bp and Condensation of Fmoc-Gln(Trt)-OH Fmoc-His(Trt)-Gly-NH-Bp (851 mg) obtained in Example 11 was dissolved in chloroform (5 ml), and diethylamine (817 µl, 7.88 mmol) was added dropwise in an ice bath. The mixture was warmed to room temperature, acetonitrile (1.5 ml) was added and the mixture was stirred for 1.5 hr. Diethylamine (544 µl, 5.44 mmol) was added and the mixture was stirred for 1 hr. Diethylamine (544 µl, 5.44 mmol) was further added and the mixture was stirred for 1 hr. The solvent was evaporated, and the residue was precipitated with methanol. The obtained crystals were slurry washed with acetonitrile to give wet crystals of His(Trt)-Gly-NH-Bp. The obtained wet crystals were dissolved in chloroform (8 ml), Fmoc-Gln(Trt)-OH(347 mg, 568 µmol) and HOBt (7.68 mg, 56.8 µmol) were added at room temperature and EDC.HCl (120 mg, 626 µmol) was added in an ice bath, and the mixture was stirred at room temperature overnight. The solvent was evaporated, and the residue was precipitated with methanol to give Fmoc-Gln(Trt)-His(Trt)-Gly-NH-Bp (952 mg, yield 90% vs Bp-OH)).

Example 13

Synthesis of 4,4-di(12-docosoxydodecyloxy)benzophenone

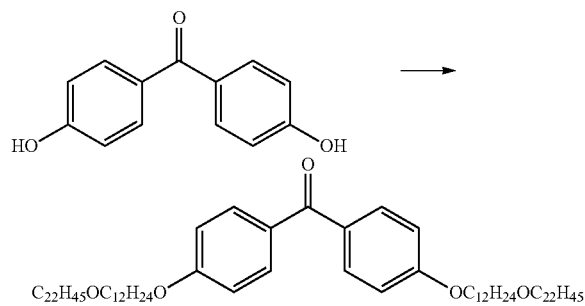

To 4,4-dihydroxybenzophenone (196 mg, 915 μmol) were added DMF (20 ml), 1-(12-bromododecyloxy)docosane (1.1 g, 1.91 mmol) and potassium carbonate (379 mg, 2.74 mmol), and the mixture was stirred at 90° C. overnight. The reaction mixture was cooled to room temperature, and 0.5N hydrochloric acid (20 ml) and chloroform (20 ml) were added. After stirring for a while, the aqueous layer was removed, and the organic layer was washed with water (10 ml)×2. The organic layer was evaporated under reduced pressure, and the residue was washed with methanol. The precipitate was collected by filtration to give 4,4-di(12-docosoxydodecyloxy)benzophenone (1.04 g, 867 μmol, 95%).

$^1$H-NMR (CDCl$_3$/300 MHz)

0.88 (6H, t, J=6.9, C$_{21}$H$_{42}$—CH$_3$) 1.15-1.60 (116H, br, Alkyl-H) 1.81 (4H, m, Ar—O—CH$_2$—CH$_2$—) 3.39 (8H, t, J=6.9, C$_{11}$H$_{22}$—CH$_2$—O—CH$_2$—C$_{21}$H$_{43}$) 4.03 (4H, t, J=6.6, Ar—O—CH$_2$—C$_{11}$H$_{22}$) 6.94 (4H, d, J=8.7, Ph C3,5-H) 7.77 (4H, d, J=8.7, Ph C2,6-H)

Example 14

Synthesis of 4,4-di(12-docosoxydodecyloxy)benzhydrol

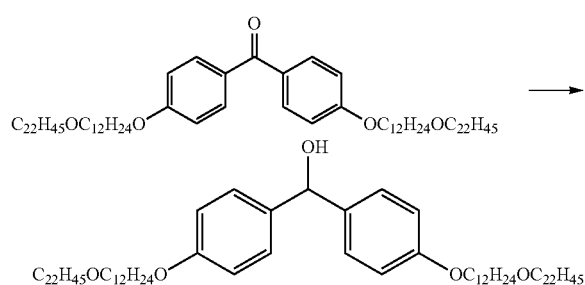

4,4-Di(12-docosoxydodecyloxy)benzophenone (1.04 g, 867 μmol) was dissolved in chloroform (20 ml), and methanol (2 ml) and sodium borohydride (98 mg, 2.60 mmol) were added, and the mixture was stirred at 60° C. for 4 hr. The reaction mixture was cooled to room temperature, 0.5N hydrochloric acid (20 ml) was added and the mixture was stirred for a while. The aqueous layer was removed, and the organic layer was washed with water (10 ml)×2. The organic layer was evaporated under reduced pressure, and the residue was crystallized from methanol to give 4,4-di(12-docosoxydodecyloxy)benzhydrol (1.03 g, 857 μmol, 98%).

$^1$H-NMR (CDCl$_3$/300 MHz)

0.88 (6H, t, J=6.9, C$_{21}$H$_{42}$—CH$_3$) 1.10-1.65 (116H, br, Alkyl-H) 1.76 (4H, m, Ar—O—CH$_2$—CH$_2$—) 2.05 (1H, s, OH) 3.38 (8H, t, J=6.6, C$_{11}$H$_{22}$—CH$_2$—O—CH$_2$—C$_{21}$H$_{43}$) 4.03 (4H, t, J=6.6, Ar—O—CH$_2$—C$_{11}$H$_{22}$) 5.75 (1H, s, CH—OH) 6.85 (4H, d, J=8.4, Ph C3,5-H) 7.26 (4H, C2,6-H)

Example 15

Synthesis of chloro-bis[4-(12-docosoxydodecyloxy)phenyl]methane

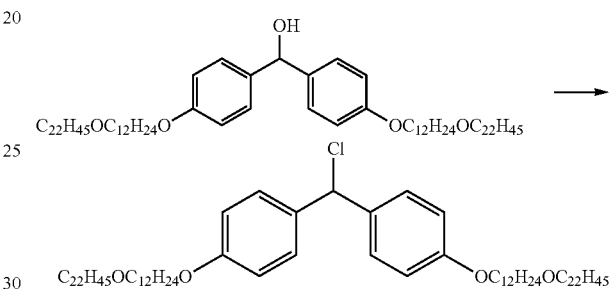

4,4-Di(12-docosoxydodecyloxy)benzhydrol (152 mg, 126 μmol) was dissolved in chloroform (2 ml), DMF (2 μl, 26 μmol) and thionyl chloride (43 μl, 595 μmol) were added, and the mixture was stirred at room temperature for 1 hr. The reaction mixture was evaporated under reduced pressure, and the residue was crystallized from acetonitrile to give chloro-bis[4-(12-docosoxydodecyloxy)phenyl]methane (142 mg, 116 μmol, 92%).

$^1$H-NMR (CDCl$_3$/300 MHz)

0.88 (6H, t, J=6.9, C$_{21}$H$_{42}$—CH$_3$) 1.10-1.65 (116H, br, Alkyl-H) 1.76 (4H, m, Ar—O—CH$_2$—CH$_2$—) 3.39 (8H, t, J=6.6, C$_{11}$H$_{22}$—CH$_2$—O—CH$_2$—C$_{21}$H$_{43}$) 3.93 (4H, t, J=6.6, Ar—O—CH$_2$—C$_{11}$H$_{22}$) 6.10 (1H, s, CH—Cl) 6.84 (4H, d, J=8.7, Ph C3,5-H) 7.30 (4H, d, J=8.7, Ph C2,6-H)

Example 16

Synthesis of azido-bis[4-(12-docosoxydodecyloxy)phenyl]methane

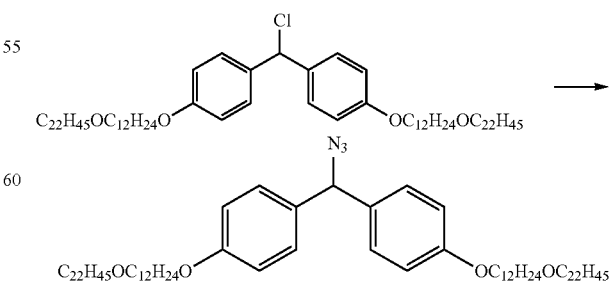

To chloro-bis[4-(12-docosoxydodecyloxy)phenyl]methane (80.9 mg, 66.3 μmol) were added DMF (3 ml), chloroform (1 ml) and sodium azide (40 mg, 621 μmol) and the mixture was stirred at 80° C. for 6 hr. Sodium azide (40.4 mg, 621 μmol) was added, and the mixture was stirred at 90° C. for 1.5 hr. The mixture was cooled to room temperature. Chloroform (2 ml) was added, and the mixture was washed with purified water (3 ml)×3 for partitioning, and the organic layer was evaporated under reduced pressure. The residue was crystallized from acetonitrile to give azido-bis[4-(12-docosoxydodecyloxy)phenyl]methane (72.0 mg, 58.7 μmol, 89%).

$^1$H-NMR (CDCl$_3$/300 MHz)

0.88 (6H, t, J=6.6, C$_{21}$H$_{42}$—CH$_3$) 1.15-1.65 (116H, br, Alkyl-H) 1.76 (4H, m, Ar—O—CH$_2$—CH$_2$—) 3.39 (8H, t, J=6.6, C$_{11}$H$_{22}$—CH$_2$—O—CH$_2$—C$_{21}$H$_{43}$) 3.93 (4H, t, J=6.6, Ar—O—CH$_2$—C$_{11}$H$_{22}$) 5.61 (1H, s, CH—N$_3$l) 6.86 (4H, d, J=8.7, Ph C3,5-H) 7.19 (4H, d, J=8.7, Ph C2,6-H)

Example 17

Synthesis of amino-bis[4-(12-docosoxydodecyloxy)phenyl]methane

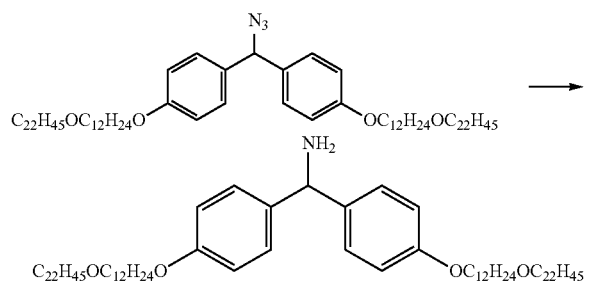

To azido-bis[4-(12-docosoxydodecyloxy)phenyl]methane (72.0 mg, 58.7 μmol) were added toluene (2 ml), purified water (2 ml) and triphenylphosphine (29 mg, 110 μmol) and the mixture was vigorously stirred at 45° C. for 3 hr and 60° C. for 3.5 hr. The reaction mixture was cooled to room temperature, and 10% aqueous sodium hydrogen carbonate (2 ml) was added. After stirring for a while, toluene (8 ml) was added and the aqueous layer was discarded. The organic layer was washed with purified water (10 ml)×2. The organic layer was evaporated under reduced pressure, and the residue was crystallized from acetonitrile, and the obtained crystals were washed with purified water to give amino-bis[4-(12-docosoxydodecyloxy)phenyl]methane (44 mg, 36.5 μmol, 62%).

$^1$H-NMR (CDCl$_3$/300 MHz)

0.88 (6H, t, J=6.9, C$_{21}$H$_{42}$—CH$_3$) 1.15-1.65 (116H, br, Alkyl-H) 1.75 (4H, m, Ar—O—CH$_2$—CH$_2$—) 3.38 (8H, t, J=6.6, C$_{11}$H$_{22}$—CH$_2$—O—CH$_2$—C$_{21}$H$_{43}$) 3.91 (4H, t, J=6.6, Ar—O—CH$_2$—C$_{11}$H$_{22}$) 6.10 (1H, s, CH—NH$_2$) 6.82 (4H, d, J=8.7, Ph C3,5-H) 7.25 (4H, d, J=8.7, Ph C2,6-H)

Example 18

Fmoc-amination of 4,4-di(12-docosoxydodecyloxy)benzhydrol

To 4,4-di(12-docosoxydodecyloxy)benzhydrol (hereinafter OH-Dpm (OC$_{12}$OC$_{22}$), 482 mg, 401 μmol) were added toluene (10 ml), Fmoc-NH$_2$ (101 mg, 422 μmol) and methanesulfonic acid (3.4 μl, 52.5 μmol), and the mixture was stirred at 100° C. for 3.5 hr. The reaction mixture was cooled to room temperature, 2.5% aqueous sodium hydrogen carbonate (6 ml) was added, and the mixture was stirred for a while. The aqueous layer was discarded, and the organic layer was washed with purified water (6 ml)×2. The organic layer was evaporated under reduced pressure, and the residue was crystallized from methanol to give Fmoc-NH-Dpm (OC$_{12}$OC$_{22}$) (533 mg, 374 mol, 93%).

$^1$H-NMR (CDCl$_3$/300 MHz)

0.88 (6H, t, J=6.9, C$_{21}$H$_{42}$—CH$_3$) 1.15-1.65 (116H, br, Alkyl-H) 1.76 (4H, m, Ar—O—CH$_2$—CH$_2$—) 3.38 (8H, t, J=6.6, C$_{11}$H$_{22}$—CH$_2$—O—CH$_2$—C$_{21}$H$_{43}$) 3.93 (4H, t, J=6.6, Ar—O—CH$_2$—C$_{11}$H$_{22}$) 4.21 (1H, br, s, fluorene C9-H) 4.43 (2H, br, m, fluorene-CH$_2$—O) 5.23 (1H, br, Fmoc-NH— or Fmoc-NH—CH) 5.85 (1H, br, Fmoc-NH— or Fmoc-NH—CH) 6.84 (4H, d, J=8.7, Ph C3,5-H) 7.11 (4H, d, J=8.7, Ph C2,6-H) 7.25-7.35 (2H, br, fluorene C2,7-H) 7.39 (2H, br, fluorene C3,6-H) 7.59 (2H, br, fluorene C1,8-H) 7.75 (2H, br, fluorene C4,5-H)

Example 19

Synthesis of amino-bis[4-(12-docosoxydodecyloxy)phenyl]methane

To 2% 1,8-diazabicyclo[5.4.0]-7-undecene(DBU)-dichloromethane solution (10 ml) was added Fmoc-NH-Dpm (OC$_{12}$OC$_{22}$) (533 mg, 374 μmol), and the mixture was stirred at room temperature for 2 hr. 1N Hydrochloric acid (2 ml) was added, and dichloromethane was evaporated under reduced pressure. To the residue were added 5% aqueous sodium hydrogen carbonate (10 ml) and acetonitrile (5 ml) for crystallization. The crystals were collected by filtration and washed with water and acetonitrile to give NH$_2$-Dpm (OC$_{12}$OC$_{22}$) (660 mg, 99%).

Example 20

Synthesis of Fmoc-Cys(Trt)-NH-Dpm(OC$_{12}$OC$_{22}$)

To NH$_2$-Dpm(OC$_{12}$OC$_{22}$) was added chloroform (5 ml), Fmoc-Cys(Trt)-OH (229 mg, 391 μmol) and HOBt (5.3 mg, 39 μmol) were added at room temperature and EDC.HCl (82 mg, 429 μmol) was added in an ice bath. The mixture was warmed to room temperature and stirred for 4.5 hr. The reaction mixture was evaporated, and the residue was precipitated with methanol to give Fmoc-Cys(Trt)-NH-Dpm(OC$_{12}$OC$_{22}$) (666 mg, 94% vs HO-Dpm (OC$_{12}$OC$_{22}$)).

$^1$H-NMR (CDCl$_3$/300 MHz)

0.88 (6H, t, J=6.9, C$_{21}$H$_{42}$—CH$_3$) 1.00-1.65 (116H, br, Alkyl-H) 1.72 (4H, m, Ar—O—CH$_2$—CH$_2$—) 2.60 (1H, dd, J=6.0, 13.5, —S—CH$_2$—) 2.73 (1H, dd, J=7.5, 13.5, —S—CH$_2$—) 3.38 (8H, t, J=6.6, C$_{11}$H$_{22}$—CH$_2$—O—CH$_2$—C$_{21}$H$_{43}$) 3.70-3.95 (5H, br, Ar—O—CH$_2$—C$_{11}$H$_{22}$, Fmoc-NH—CH—) 4.14 (1H, br, s, fluorene C9-H) 4.34 (2H, br, m, fluorene-CH$_2$—O) 5.02 (1H, br, Fmoc-NH—) 5.99 (1H, br, Cys-NHCH—Ar$_2$ or Cys-NHCH—Ar$_2$) 6.27 (1H, br, Cys-NHCH—Ar$_2$ or Cys-NHCH—Ar$_2$) 6.74 (4H, d, J=8.1, Ph C3,5-H) 7.02 (4H, d, J=8.7, Ph C2,6-H) 7.15-7.45 (15H, m, fluorene C2,3,6,7-H, Trt) 7.52 (2H, br, fluorene C1,8-H) 7.73 (2H, br, fluorene C4,5-H)

Example 21

Removal of Fmoc from Fmoc-Cys(Trt)-NH-Dpm (OC$_{12}$OC$_{22}$) and Condensation of Fmoc-Pro-OH Fmoc-Cys(Trt)-NH-Dpm(OC$_{12}$OC$_{22}$) (666 mg) was dissolved in chloroform (5 ml), and diethylamine (747 μl, 7.20 mmol) was added dropwise in an ice bath. The mixture was warmed to room temperature, acetonitrile (2.5 ml) and chloroform (2 ml) were added and the mixture was stirred for 2 hr. Diethylamine (373 μl, 3.60 mmol) was added and the mixture was stirred for 1.5 hr. Diethylamine (373 μl, 3.60 mmol) was added and the mixture was stirred for 1.5 hr. Further, diethylamine (187 μl, 1.80 mmol) was added and the mixture was stirred for 1 hr. The reaction mixture was evaporated, and the residue was precipitated with acetonitrile to give wet crystals of Cys (Trt)-NHDpm($OC_{12}OC_{22}$). The obtained wet crystals were dissolved in chloroform (5 ml), Fmoc-Pro-OH (134 mg, 397 μmol) and HOBt (5.4 mg, 39.6 μmol) were added at room temperature, and EDC.HCl (84 mg, 436 μmol) was added in an ice bath. The mixture was warmed to room temperature, stirred overnight, and evaporated. The residue was precipitated with methanol to give Fmoc-Pro-Cys(Trt)-NH-Dpm ($OC_{12}OC_{22}$) (720 mg, 96% vs HO-Dpm ($OC_{12}OC_{22}$)).

Example 22

Removal of Fmoc from Fmoc-Pro-Cys(Trt)-NH-Dpm($OC_{12}OC_{22}$) and Condensation of Fmoc-Trp(Boc)-OH Fmoc-Cys(Trt)-NH-Dpm($OC_{12}OC_{22}$) (720 mg) was dissolved in chloroform (5 ml), and diethylamine (747 μl, 7.20 mmol) was added dropwise in an ice bath. The mixture was warmed to room temperature and stirred for 2 hr. Diethylamine (747 μl, 7.20 mmol) was added and the mixture was stirred for 1.5 hr, diethylamine (373 μl, 3.60 mmol) was added and the mixture was stirred for 1 hr, and further, diethylamine (373 μl, 3.60 mmol) was added and the mixture was stirred for 0.5 hr. The reaction mixture was evaporated, and the residue was precipitated with acetonitrile to give wet crystals of Pro-Cys (Trt)-NH-Dpm($OC_{12}OC_{22}$). The obtained wet crystals were dissolved in chloroform (5 ml), Fmoc-Trp(Boc)-OH (223 mg, 423 μmol) and HOBt (5.7 mg, 42.5 μmol) were added at room temperature and EDC.HCl (90 mg, 467 μmol) was added in an ice bath. The mixture was warmed to room temperature, stirred overnight and evaporated. The residue was precipitated with methanol to give Fmoc-Trp(Boc)-Pro-Cys (Trt)-NH-Dpm($OC_{12}OC_{22}$) (765 mg, yield 89% vs HO-Dpm($OC_{12}OC_{22}$)).

Example 23

Removal of Fmoc from Fmoc-Trp(Boc)-Pro-Cys (Trt)-NH-Dpm($OC_{12}OC_{22}$) and Condensation of Fmoc-Asp(tBu)-OH Fmoc-Trp(Boc)-Pro-Cys (Trt)-NH-Dpm($OC_{12}OC_{22}$) (765 mg) was dissolved in chloroform (5 ml), and diethylamine (1.10 ml, 10.6 mmol) was added dropwise in an ice bath. The mixture was warmed to room temperature and stirred for 2 hr. Diethylamine (550 μl, 5.30 mmol) was added and the mixture was further stirred for 3 hr. The reaction mixture was evaporated, and the residue was precipitated with acetonitrile to give wet crystals of Trp(Boc)-Pro-Cys (Trt)-NH-Dpm ($OC_{12}OC_{22}$). The obtained wet crystals were dissolved in chloroform (5 ml), Fmoc-Asp(tBu)-OH (161 mg, 391 μmol) and HOBt (5.3 mg, 39.1 μmol) were added at room temperature and EDC.HCl (83 mg, 429 μmol) was added in an ice bath. The mixture was cooled to room temperature, stirred overnight and evaporated. The residue was precipitated with methanol to give Fmoc-Asp(tBu)-Trp(Boc)-Pro-Cys(Trt)-NH-Dpm($OC_{12}OC_{22}$) (SEQ ID NO:1) (816 mg, yield 88% vs HO-Dpm($OC_{12}OC_{22}$)).

Fmoc-Asp(tBu)-Trp (Boc)-Pro-Cys(Trt)-NH-Dpm ($OC_{12}OC_{22}$) (300 mg) was stirred in a mixture (3 ml) of TFA:TIPS (triisopropylsilane):$H_2O$=95:2.5:2.5. After completion of the reaction, MTBE (methyl t-butyl ether) was added and the precipitate was collected by filtration. The precipitate was washed twice with a mixed solution of THF/cyclohexane (3:7, 5 ml) with heating. The precipitate was collected by filtration and dried under reduced pressure to give crude crystals of Fmoc-Asp-Trp-Pro-Cys-$NH_2$ (SEQ ID NO:2) (141 mg). ESI-MS: Calcd 741.3 [M+H]$^+$. Found 741.0 [M+H]$^+$.

Example 24

Removal of Anchor (Synthesis of (H-Phe-Cys(Acm)-Thr(tBu)-$NH_2$)

In the same manner as in Examples 6-9 and using a benzhydrol type anchor (Dpm($OC_{22}$)$_2$—OH), H-Phe-Cys (Acm)-Thr(tBu)-NH-Dpm($OC_{22}$)$_2$ was prepared by the following steps.

Fmoc-Thr(tBu)-$NH_2$ was introduced into Dpm($OC_{22}$)$_2$—OH, Fmoc was removed from the obtained Fmoc-Thr(tBu)-NH-Dpm($OC_{22}$)$_2$, and then Fmoc-Cys(Acm)-OH was condensed to give Fmoc-Cys(Acm)-Thr(tBu)-NH-Dpm($OC_{22}$)$_{22}$. Fmoc was removed from the obtained Fmoc-Cys (Acm)-Thr (tBu)-NH-Dpm ($OC_{22}$)$_{22}$, and then Fmoc-Phe-OH was condensed to give Fmoc-Phe-Cys(Acm)-Thr(tBu)-NH-Dpm($OC_{22}$)$_{22}$. Fmoc was removed from the obtained Fmoc-Phe-Cys(Acm)-Thr(tBu)-NH-Dpm ($OC_{22}$)$_{22}$ to give H-Phe-Cys (Acm)-Thr (tBu)-NH-Dpm ($OC_{22}$)$_2$.

H-Phe-Cys(Acm)-Thr(tBu)-NH-Dpm($OC_{22}$)$_2$ (102 mg) was stirred in a mixture (1 ml) of TFA:TIPS(triisopropylsilane):$H_2O$=95:2.5:2.5. After completion of the reaction, the precipitate was filtered, and the filtrate was concentrated. MTBE (methyl t-butylether) was added and the mixture was stirred. The precipitate was collected by filtration to give crude crystals of Phe-Cys(Acm)-Thr-$NH_2$ TFA salt (35 mg).

ESI-MS: Calcd 440.2 [M+H]$^+$. Found 440.0 [M+H]$^+$.

Example 25

Synthesis of N-benzyl-[bis(4-docosyloxyphenyl)]methylamine

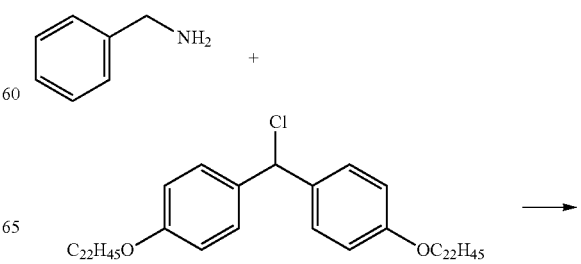

-continued

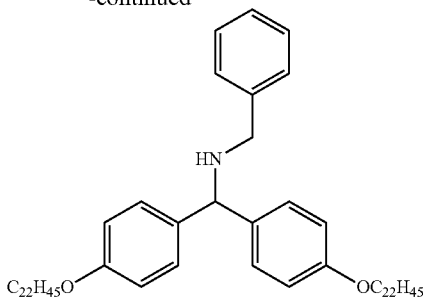

To chloro-bis(4-docosyloxyphenyl)methane (75.9 mg, 89.1 μmol) were added chloroform (1 ml), benzylamine (29.1 μl, 267 μmol) and N-ethyldiisopropylamine (45.7 μl, 267 μmol), and the mixture was stirred at room temperature overnight. The reaction mixture was warmed to 50° C. and stirred for 1 hr. The mixture was cooled to room temperature again, and washed successively with 0.5N hydrochloric acid, 10% aqueous sodium hydrogen carbonate and 20% brine. The organic layer was dehydrated with anhydrous sodium sulfate, chloroform was evaporated, and the residue was precipitated with methanol to give N-benzyl-[bis(4-docosyloxyphenyl)] methylamine (72 mg, 87%).

Example 26

Synthesis of 4-(3,4,5-tris-octadecyloxy-cyclohexylmethoxy)-benzaldehyde 26-1: synthesis of (3,4,5-tris-octadecyloxy-cyclohexyl)-methanol Methyl trialkoxy-cyclohexylcarboxylate (2.87 g, 3.03 mmol) was dissolved in dehydrated THF (30 mL), DIBAL-H (9 mmol) was added and the mixture was stirred at room temperature for 30 min. 1N Hydrochloric acid (10 mL) was added and THF was evaporated under reduced pressure. Chloroform (30 mL) and 1N hydrochloric acid (30 mL) were added for partitioning. The organic layer was recovered and the solvent was evaporated. The residue was crystallized from methanol and the crystals were filtered and thoroughly washed with 1N hydrochloric acid and methanol to give (3,4,5-tris-octadecyloxy-cyclohexyl)-methanol (2.58 g, 2.81 mmol, 93%).

$^1$H NMR (CDCl$_3$/300 MHz)

δ=0.88 (9H, t, J=6.9 Hz, OC$_{18}$H$_{37}$ C18-H) 1.1-1.8 (101H, br, Cyclohexyl C1,2,6-H, OC$_{18}$H$_{37}$ C2-17-H) 3.14 (2H, m, Cyclohexyl C3,5-H) 3.35-3.57 (6H, m, 3,5-OC$_{18}$H$_{37}$ C1-H, HO—CH$_2$—) 3.67 (2H, t, J=6.8 Hz, 4-OC$_{18}$H$_{37}$ C1-H) 3.90 (1H, s, Cyclohexyl C4-H)

26-2: synthesis of 4-(3,4,5-tris-octadecyloxy-cyclohexylmethoxy)-benzaldehyde

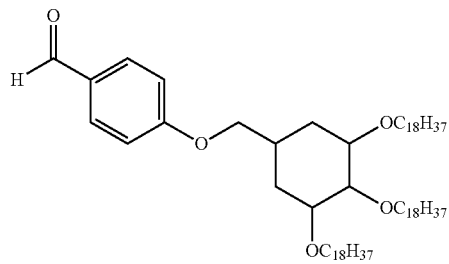

(3,4,5-Tris-octadecyloxy-cyclohexyl)-methanol (283 mg, 308 μmol), 4-hydroxy-benzaldehyde (56 mg, 459 μmol), triphenylphosphine (121 mg, 461 μmol) dissolved in dehydrated THF (5.5 mL), DIED (93.3 μL, 472 μmol) was added and the mixture was stirred for 40 min. 4-Hydroxy-benzaldehyde, triphenylphosphine and DIED (each 153 μmol) were added and the mixture was stirred overnight. Triphenylphosphine and DIED (each 306 μmol) were added and the mixture was stirred for 2.5 hr. THF was evaporated, and 90% aqueous acetonitrile (6 ml) was added to the residue to allow crystallization. The crystals were collected by filtration and thoroughly washed with acetonitrile to give crude crystals of 4-(3,4,5-tris-octadecyloxy-cyclohexylmethoxy)-benzaldehyde. The crude crystals were purified by silica gel column chromatography (hexane:ethyl acetate=20:1) to give the object compound (130 mg, 127 μmol, 41%).

4-Cyclohexylmethoxy-PhCHO $^1$H NMR (CDCl$_3$/300 MHz)

δ=0.88 (9H, t, J=6.9 Hz, OC$_{18}$H$_{37}$ C18-H) 1.1-1.9 (101H, br, Cyclohexyl C1,2,6-H, OC$_{18}$H$_{37}$C2-17-H) 3.18 (2H, d, J=10.4 Hz, Cyclohexyl C3,5-H) 3.48 (4H, m, 3,5-OC$_{18}$H$_{37}$ C1-H) 3.68 (2H, t, J=6.7 Hz, 4-OC$_{18}$H$_{37}$ C1-H) 3.91 (2H, d, J=5.7 Hz, Cyclohexyl C4-H, PhO-CH$_2$—) 3.94 (1H, s, Cyclohexyl C4-H) 6.98 (2H, d, J=8.7 Hz, Ph C3,5-H) 7.82 (2H, d, J=8.7 Hz, Ph C2,6-H) 9.88 (1H, s, Ph-CHO)

Example 27

Synthesis of (4-methoxy-phenyl)-[4-(3,4,5-tris-octadecyloxy-cyclohexylmethoxy)-phenyl]-methanol

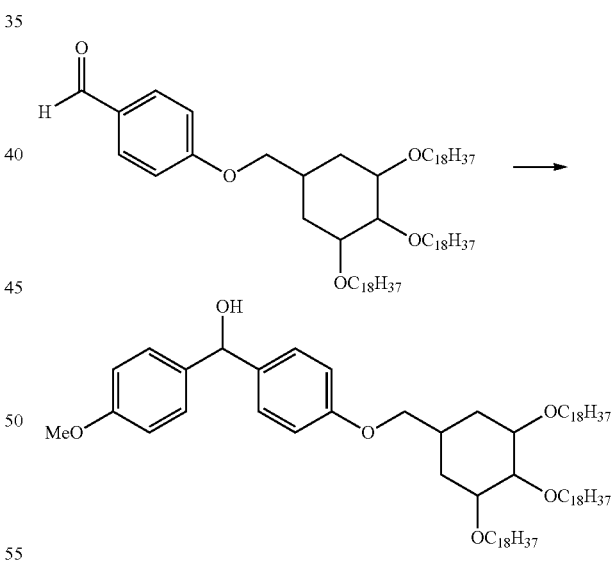

4-(3,4,5-Tris-octadecyloxy-cyclohexylmethoxy)-benzaldehyde (130 mg, 127 μmol) was dissolved in dehydrated THF (2 mL), 4-methoxy-phenyl-magnesiumbromide (350 μmol) was added, and the mixture was stirred at 40° C. for 1.5 hr. After evaporation of the solvent, 1N hydrochloric acid (5 mL) was added to the residue to allow crystallization. The crystals were filtered, and thoroughly washed with hydrochloric acid, water and methanol in this order to give (4-methoxy-phenyl)-[4-(3,4,5-tris-octadecyloxy-cyclohexylmethoxy)-phenyl]-methanol (110 mg, 97.2 μmol, 96%).

$^1$H NMR (CDCl$_3$/300 MHz)

δ=0.88 (9H, t, J=6.6 Hz, OC$_{18}$H$_{37}$ C18-H) 1.1-1.9 (101H, br, Cyclohexyl C1,2,6-H, OC$_{18}$H$_{37}$ C2-17-H) 2.05 (1H, s, HO—CHPh$_2$) 3.16 (2H, d, J=10.2 Hz, Cyclohexyl C3,5-H) 3.46 (4H, m, 3,5-OC$_{18}$H$_{37}$C1-H) 3.67 (2H, t, J=6.7 Hz, 4-OC$_{18}$H$_{37}$ C1-H) 3.79 (5H, m, 4-OCH$_2$—, 4'-OCH$_3$) 3.91 (1H, s, Cyclohexyl C4-H) 5.77 (1H, s, HOCHPh$_2$) 6.98 (2H, d, J=8.7 Hz, Ph C3,5-H) 7.82 (2H, d, J=8.7 Hz, Ph C2,6-H) 9.88 (1H, s, Ph-CHO)

Example 28

Synthesis of ethyl {(4-methoxy-phenyl)-[4-(3,4,5-tris-octadecyloxy-cyclohexylmethoxy)-phenyl]-methyl}-carbamate

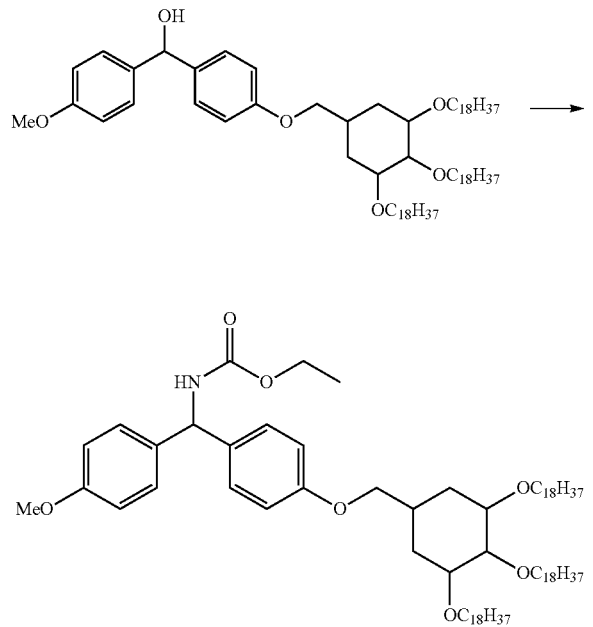

To (4-methoxy-phenyl)-[4-(3,4,5-tris-octadecyloxy-cyclohexylmethoxy)-phenyl]-methanol (110 mg, 97.2 μmol) were added toluene (2 mL), ethyl carbamate (17.8 mg, 200 μmol), and methanesulfonic acid (1 μL, 15 μmol) and the mixture was stirred at 110° C. for 2 hr. The reaction mixture was cooled to room temperature, sodium carbonate (5 mg, 47 μmol) was added and the solvent was evaporated. The residue was crystallized from methanol (5 mL) to give ethyl{(4-methoxy-phenyl)-[4-(3,4,5-tris-octadecyloxy-cyclohexyl-methoxy)-phenyl]-methyl}-carbamate (127 mg, 100%).

4-Cyclohexylmethoxy-4'-OMe-Dpm-NHCOOEt $^1$H NMR (CDCl$_3$/300 MHz)

δ=0.88 (9H, t, J=6.6 Hz, OC$_{18}$H$_{37}$ C18-H) 1.1-1.9 (104H, br, Cyclohexyl C1,2,6-H, OC$_{18}$H$_{37}$C2-17-H, COOCH$_2$CH$_3$) 3.17 (2H, d, J=10.3 Hz, Cyclohexyl C3,5-H) 3.46 (4H, m, 3,5-OC$_{18}$H$_{37}$ C1-H) 3.67 (2H, t, J=6.7 Hz, 4-OC$_{18}$H$_{37}$ C1-H) 3.79 (5H, m, 4-OCH$_2$—, 4'-OCH$_3$) 3.92 (1H, s, Cyclohexyl C4-H) 4.12 (2H, qua, J=7.1 Hz, COOCH$_2$CH$_3$) 5.15 (1H, s, —NHCHPh$_2$) 5.84 (1H, d, J=7.2 Hz, —NHCO—) 6.83 (4H, m, Ph C3,3',5,5'-H) 7.13 (4H, m, Ph C2,2',6,6'-H)

Example 29

Synthesis of {(4-methoxy-phenyl)-[4-(3,4,5-tris-octadecyloxy-cyclohexylmethoxy)-phenyl]-methyl}-amine

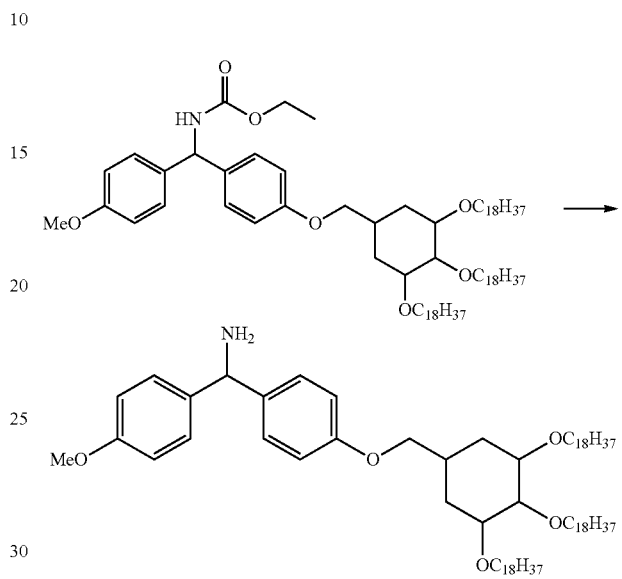

To crude crystals (127 mg) of ethyl{(4-methoxy-phenyl)-[4-(3,4,5-tris-octadecyloxy-cyclohexylmethoxy)-phenyl]-methyl}-carbamate were added toluene (2 mL), ethanol (2 mL) and sodium hydroxide (21 mg, 525 μmol) and the mixture was stirred at 100° C. for 2 hr. The reaction mixture was cooled to room temperature, toluene (2 mL) was added, and washed with water (4 mL×3 times) to allow partitioning. The organic layer was evaporated, and the residue was crystallized from acetonitrile (5 mL) to give {(4-methoxy-phenyl)-[4-(3,4,5-tris-octadecyloxy-cyclohexylmethoxy)-phenyl]-methyl}-amine (123 mg, 100% vs —OH form).

$^1$H NMR (CDCl$_3$/300 MHz)

δ=0.88 (9H, t, J=6.4 Hz, OC$_{18}$H$_{37}$ C18-H) 1.1-1.9 (103H, br, Cyclohexyl C1,2,6-H, OC$_{18}$H$_{37}$ C2-17-H, —NH$_2$) 3.16 (2H, d, J=10.4 Hz, Cyclohexyl C3,5-H) 3.46 (4H, m, 3,5-OC$_{18}$H$_{37}$ C1-H) 3.67 (2H, t, J=6.6 Hz, 4-OC$_{18}$H$_{37}$ C1-H) 3.79 (5H, m, 4-OCH$_2$—, 4'-OCH$_3$) 3.92 (1H, s, Cyclohexyl C4-H) 5.11 (1H, s, H$_2$NCHPh$_2$) 6.83 (4H, m, Ph C3,3',5,5'-H) 7.25 (4H, m, Ph C2,2',6,6'-H)

Example 30

Synthesis of ethyl [bis-(4-docosoxy-phenyl)-methyl]carbamate

To bis-(4-docosoxy-phenyl)-methanol (28.5 g, 34.2 mmol) were added toluene (350 mL), ethyl carbamate (6.1 g, 68.5 mmol) and methanesulfonic acid (333 μL, 5.14 mmol) and the mixture was stirred at 110° C. for 2 hr. Methanesulfonic acid (333 μL, 5.14 mmol) was added and the mixture was stirred for 30 min. After stirring, the reaction mixture was cooled to room temperature, sodium carbonate (1.1 g, 8.73 mmol) was added and the solvent was evaporated. The residue was crystallized from methanol (400 mL) to give ethyl [bis-(4-docosoxy-phenyl)-methyl]carbamate (32.1 g, 100%).

4-Cyclohexylmethoxy-4'-OMe-Dpm-NHCOOEt $^1$H NMR (CDCl$_3$/300 MHz)

δ=0.88 (6H, t, J=6.6 Hz, OC$_{22}$H$_{45}$ C22-H) 1.1-1.6 (79H, br, OC$_{22}$H$_{45}$ C3-21-H, COOCH$_2$CH$_3$) 1.75 (4H, m, OC$_{22}$H$_{45}$ C2-H) 3.92 (4H, t, J=6.5 Hz, OC$_{22}$H$_{45}$ C1-H) 4.13 (2H, qua, J=7.1 Hz, COOCH$_2$CH$_3$) 5.15 (1H, s, —NHCHPh$_2$) 5.85 (1H, d, J=6.9 Hz, —NHCO—) 6.83 (4H, d, J=8.6 Hz, Ph C3,3',5,5'-H) 7.13 (4H, d, J=8.6 Hz, Ph C2,2',6,6'-H)

Example 31

Synthesis of di(4-docosoxyphenyl)methylamine

To crude crystals (31.9 g) of ethyl di(4-docosoxyphenyl) methylcarbamate were added toluene (300 mL), ethanol (200 mL) and sodium hydroxide (4.2 g, 105 mmol), and the mixture was refluxed under stirring at 100° C. Sodium hydroxide (total 9.8 g, 245 mmol) was added, and the mixture was stirred for 16 hr. The reaction mixture was cooled to room temperature, and water (300 mL), hexane (200 mL) and ethyl acetate (200 mL) were added for partitioning. The aqueous layer was discarded, and the organic layer and precipitated crystals were washed with water (300 mL×2). The organic layer and crystals were recovered. The solvent was evaporated under reduced pressure. To the residue were added water (150 mL) and acetonitrile (150 mL) to allow crystallization. The crystals were collected by filtration and thoroughly washed with water and acetonitrile to give di(4-docosoxyphenyl)methylamine (28.1 g, 33.7 mmol, 98% vs —OH).

$^1$H NMR (CDCl$_3$/300 MHz)

δ=0.88 (6H, t, J=6.6 Hz, OC$_{22}$H$_{45}$ C22-H) 1.1-1.6 (78H, br, OC$_{22}$H$_{45}$ C3-21-H, —NH$_2$) 1.75 (4H, m, OC$_{22}$H$_{45}$ C2-H) 3.92 (4H, t, J=6.6 Hz, OC$_{22}$H$_{45}$ C1-H) 5.12 (1H, s, H$_2$N—C HPh$_2$) 6.83 (4H, d, J=8.6 Hz, Ph C3,3',5,5'-H) 7.24 (4H, d, J=8.6 Hz, Ph C2,2',6,6'-H)

INDUSTRIAL APPLICABILITY

The particular compound of the present invention having a diphenylmethane skeleton can provide a compound superior in broad utility and stability, which is useful as a protecting reagent (anchor) of amino acid and/or peptide in liquid phase synthesis and the like of a peptide having a carboxamide-type C-terminal or side chain, an organic synthesis reaction method (particularly peptide liquid phase synthesis method) using the compound, and a kit for peptide liquid phase synthesis containing the compound.

In other words, since the particular compound having a diphenylmethane skeleton dissolves only in halogen solvents, THF and the like, and scarcely dissolves in polar organic solvents, the compound can be easily precipitated in methanol and the like. In addition, peptide chain length can be elongated by repeating an operation including reaction in a halogen solvent using the compound as an anchor of the C-terminal or side chain during peptide liquid phase synthesis, followed by precipitation with methanol etc. to remove impurities. Furthermore, after deprotection by setting acidic conditions and the like, the C-terminal etc. can be led to carboxamide. Using the method of the present invention, various active pharmaceutical ingredient (API) starting materials, intermediates and final products can be obtained conveniently.

The invention claimed is:

1. A method of producing a peptide, comprising:
   (a) condensing a diphenylmethane compound represented by formula (I)

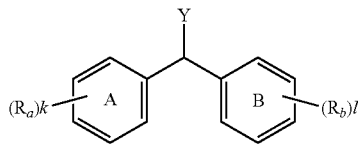

wherein
   Y is a hydroxyl group or a —NHR group, where R is a hydrogen atom, an alkyl group, or an aralkyl group;
   k and l are each independently an integer of 0 to 5 and k+l is not 0;
   each $R_a$ in the number of k and each $R_b$ in the number of l are independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
   ring A optionally further has substituent(s) besides $R_a$; and ring B optionally further has substituent(s) besides $R_b$;
   with a —CONHR group of an N-protected amino acid or N-protected peptide having a —CONHR group, wherein R is a hydrogen atom, an alkyl group or an aralkyl group, or
   with a —COOH group of an N-protected amino acid or an N-protected peptide having a —COOH group to produce a C-diphenylmethane-protected amino acid or a C-diphenylmethane-protected peptide;
   (b) deprotecting the N-terminal of the C-diphenylmethane-protected amino acid or C-diphenylmethane-protected peptide, to produce an N-unprotected amino acid or N-unprotected peptide;
   (c) condensing the N-terminal of the N-unprotected amino acid or N-un-protected peptide with an N-protected amino acid or N-protected peptide, to obtain an elongated peptide; and
   (d) isolating the elongated peptide.

2. The method of claim 1, which is conducted in a liquid phase.

3. The method of claim 1, wherein Y is a hydroxyl group.

4. The method of claim 1, wherein Y is a —NHR group.

5. The method of claim 1, wherein, in the organic group(s) in the number of (k+l), the total carbon number of the aliphatic hydrocarbon groups is 18 to 200.

6. The method of claim 1, wherein the aliphatic hydrocarbon group independently has a carbon number of not less than 5.

7. The method of claim 1, wherein the aliphatic hydrocarbon group independently has a carbon number of 5 to 60.

8. The method of claim 1, wherein the organic group is independently bonded directly to ring A or ring B by a carbon-carbon bond or via —O—, —S—, —COO—, —OCONH— or —CONH—.

9. The method of claim 8, wherein the organic group is bonded to the 4-position of ring A or ring B via —O—.

10. The method of claim 1, wherein the organic group having an aliphatic hydrocarbon group is independently selected from the group consisting of a group represented by formula (a):

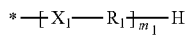
(a)

wherein
* indicates the position of a bond;
$m_1$ is an integer of 1 to 10;
$X_1$ in the number of $m_1$ are each independently absent or —O—, —S—, —COO—, —OCONH— or —CONH—; and
$R_1$ in the number of $m_1$ are each independently divalent aliphatic hydrocarbon groups having a carbon number of not less than 5;
a group represented by formula (b):

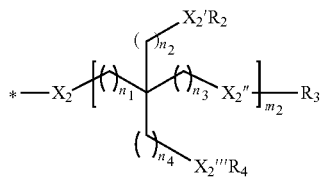
(b)

wherein
* indicates the position of a bond;
$m_2$ is an integer of 1 or 2;
$n_1$, $n_2$, $n_3$ and $n_4$ in the number of $m_2$ are each independently an integer of 0 to 2;
$X_2$, $X_2'$ in the number of $m_2$, $X_2''$ in the number of $m_2$ and $X_2'''$ in the number of $m_2$ are each independently absent, or —O—, —S—, —COO—, —OCONH— or —CONH—;
$R_2$ and $R_4$ in the number of $m_2$ are each independently a hydrogen atom, a methyl group or an aliphatic hydrocarbon group having a carbon number of not less than 5; and
$R_3$ is an aliphatic hydrocarbon group having a carbon number of not less than 5; and
a group represented by formula (e):

(e)

wherein
* indicates the position of a bond;
$m_3$ is an integer of 0 to 15;
$n_5$ is an integer of 0 to 11;
$n_6$ is an integer of 0 to 5;
$X_8$ is absent or —O—, —S—, —NHCO— or —CONH—;
$X_7$ in the number of $m_3$ are each independently absent or —O—, —S—, —COO—, —OCONH—, —NHCO— or —CONH—; and
$R_{12}$ in the number of $m_3$ are each independently a hydrogen atom, a methyl group or an aliphatic hydrocarbon group having a carbon number of not less than 5.

11. The method of claim 10, wherein, in the formula (a),
$m_1$ is 1 or 2;
$X_1$ is —O—; and
$R_1$ is a divalent aliphatic hydrocarbon group having a carbon number of 5 to 60.
12. The method of claim 10, wherein, in the formula (b),
$m_2$ is 1;
$n_1$, $n_2$, $n_3$ and $n_4$ are each independently an integer of 0 to 1;
$X_2$ is —O— or —CONH—;
$X_2'$, $X_2''$ and $X_2'''$ are each independently absent or —O—;
$R_2$ and $R_4$ are each independently a hydrogen atom, a methyl group or an aliphatic hydrocarbon group having a carbon number of 5 to 60; and
$R_3$ is an aliphatic hydrocarbon group having a carbon number of 5 to 60.
13. The method of claim 10, wherein, in the formula (e),
$m_3$ is 2 or 3;
$n_5$ is 1;
$n_6$ is 2 or 3;
$X_8$ is —O—;
$X_7$ is —O—; and
$R_{12}$ in the number of $m_3$ are each independently an alkyl group having a carbon number of 8 to 60.
14. The method of claim 10, wherein
Y is a hydroxyl group;
k and l are each independently an integer of 0 to 3; and
the organic group having an aliphatic hydrocarbon group is present at the 4-position of the ring A or ring B and is represented by
formula (a) wherein $m_1$ is 1 or 2; $X_1$ is —O—; and $R_1$ is a divalent aliphatic hydrocarbon group having a carbon number of 5 to 60, or
formula (e) wherein $m_3$ is 2 or 3; $n_5$ is 1; $n_6$ is 2 or 3; $X_8$ is —O—; $X_7$ is —O—; and $R_{12}$ in the number of $m_3$ are each independently an alkyl group having a carbon number of 14 to 30.
15. The method of claim 10, wherein
Y is a —NHR group, where R is a hydrogen atom, an alkyl group or an aralkyl group;
k and l are each independently an integer of 0 to 3;
the organic group having an aliphatic hydrocarbon group is present at the 4-position of the ring A or ring B and is represented by
formula (a) wherein $m_1$ is 1 or 2; $X_1$ is —O—; and $R_1$ is a divalent aliphatic hydrocarbon group having a carbon number of 5 to 60, or
a group represented by the formula (e) wherein $m_3$ is 2 or 3; $n_5$ is 1; $n_6$ is 2 or 3; $X_8$ is —O—; $X_7$ is —O—; and $R_{12}$ in the number of $m_3$ are each independently an alkyl group having a carbon number 14 to 30.
16. The method of claim 10, wherein the diphenylmethane compound is selected from the group consisting of
2,3,4-trioctadecanoxybenzhydrol,
[phenyl(2,3,4-trioctadecanoxyphenyl)methyl]amine,
4,4'-didocosoxybenzhydrol,
di(4-docosoxyphenyl)methylamine,
4,4-di(12-docosoxydodecyloxy)benzhydrol,
amino-bis[4-(12-docosoxydodecyloxy)phenyl]methane,
N-benzyl-[bis(4-docosyloxyphenyl)]methylamine,
(4-methoxy-phenyl)-[4-(3,4,5-tris-octadecyloxy-cyclohexylmethoxy)-phenyl]-methanol,
{(4-methoxy-phenyl)-[4-(3,4,5-tris-octadecyloxy-cyclohexylmethoxy)-phenyl-]-methyl}-amine, and
[bis-(4-docosoxy-phenyl)-methyl]-amine.

17. The method of claim 1, wherein when Y is a hydroxyl group or an —NHR— group and k+l is 1, the total carbon number of the aliphatic hydrocarbon groups is not less than 18, and
when Y is a hydroxyl group, (1) the substituent other than $R_a$ and $R_b$, that ring A and ring B optionally has is a $C_{1-6}$ alkyl group or a $C_{1-6}$ alkoxy group and (2) the aliphatic hydrocarbon groups of the respective organic groups are each independently an aliphatic hydrocarbon group having not less than 5 carbon atoms.

18. The method of claim 1, further comprising one or more repetitions of (e) to (g);
(e) deprotecting the N-terminal of said elongated peptide obtained, to obtain a N-unprotected elongated peptide;
(f) condensing the N-terminal of said N-unprotected elongated peptide with another N-protected amino acid or another N-protected peptide, to obtain a further elongated peptide; and
(g) precipitating said further elongated peptide.

19. The method of claim 1, further comprising:
(h) treating the peptide with an acid to remove a group represented by the formula (I-d):

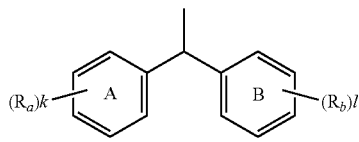

(I-d)

wherein
k and l are each independently an integer of 0 to 5 and k+l is not 0;
each Ra in the number of k and each Rb in the number of l are independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
ring A optionally further has substituent(s) besides Ra; and ring B optionally further has substituent(s) besides Rb from said further elongated peptide.

20. The method of claim 18, further comprising:
(h) removing a group represented by the formula (I-d) with an acid:

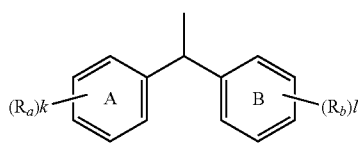

(I-d)

wherein
k and l are each independently an integer of 0 to 5 and k+l is not 0;
each Ra in the number of k and each Rb in the number of l are independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
ring A optionally further has substituent(s) besides Ra; and ring B optionally further has substituent(s) besides Rb from said further elongated peptide.

21. A method of producing a peptide, comprising:
deprotecting a diphenylmethane protecting group of a N-terminal of a C-diphenylmethane-protected amino acid or C-diphenylmethane-protected peptide with an acid,
wherein a diphenylmethane compound represented by formula (I):

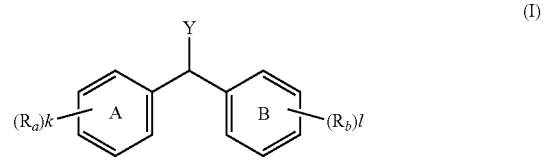

(I)

wherein
Y is a hydroxyl group or a —NHR group, where R is a hydrogen atom, an alkyl group, or an aralkyl group;
k and l are each independently an integer of 0 to 5 and k+l is not 0;
each $R_a$ in the number of k and each $R_b$ in the number of l are independently an organic group having an aliphatic hydrocarbon group, wherein, in the organic group(s) in the number of (k+l), each having an aliphatic hydrocarbon group, the total carbon number of the aliphatic hydrocarbon groups is not less than 16;
ring A optionally further has substituent(s) besides $R_a$; and ring B optionally further has substituent(s) besides $R_b$;
is condensed with a —CONHR group of an N-protected amino acid or N-protected peptide having a —CONHR group, wherein R is a hydrogen atom, an alkyl group or an aralkyl group, or
condensed with a —COOH group of an N-protected amino acid or an N-protected peptide having a —COOH group,
to produce a C-diphenylmethane-protected amino acid or a C-diphenylmethane-protected peptide;
(c) condensing the N-terminal of the N-unprotected amino acid or N-un-protected peptide with an N-protected amino acid or N-protected peptide, to obtain an elongated peptide; and
(d) isolating the elongated peptide.

* * * * *

```
                        SEQUENCE LISTING

<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asp(tBu)
<220> FEATURE:
<221> NAME/KEY: MOD_RES
<222> LOCATION: (2)..(2)
<223> OTHER INFORMATION: Trp(Boc)
<220> FEATURE:
<221> NAME/KEY: MOD_RES
<222> LOCATION: (4)..(4)
<223> OTHER INFORMATION: Cys(Trt)-NH-Dpm(OC12OC22)

<400> SEQUENCE: 1

Asp Trp Pro Cys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Fmoc-Asp
<220> FEATURE:
<223> OTHER INFORMATION: C-term amidated

<400> SEQUENCE: 2

Asp Trp Pro Cys
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Arg(Pbf)
<220> FEATURE:
<221> NAME/KEY: MOD_RES
<222> LOCATION: (2)..(2)
<223> OTHER INFORMATION: Gln(Trt)
<220> FEATURE:
<221> NAME/KEY: MOD_RES
<222> LOCATION: (3)..(3)
<223> OTHER INFORMATION: His(Trt)
<220> FEATURE:
<221> NAME/KEY: MOD_RES
<222> LOCATION: (4)..(4)
<223> OTHER INFORMATION: Gly-NH-Dpm(OC22)2

<400> SEQUENCE: 3

Arg Gln His Gly
1
```